United States Patent
Cheetham et al.

(10) Patent No.: US 6,187,802 B1
(45) Date of Patent: Feb. 13, 2001

(54) SUBSTITUTED 4-ARYLMETHYLENE-2-IMINO-2,3-DIHYDROTHIAZOLES AND DERIVATIVES AND THEIR PHARMACEUTICAL USE

(75) Inventors: Sharon Crawford Cheetham; Frank Kerrigan; Colin Gerhart Pryce Jones, all of Nottingham (GB)

(73) Assignee: Knoll Aktiengesellschaft, Ludwigshafen (DE)

( * ) Notice: Under 35 U.S.C. 154(b), the term of this patent shall be extended for 0 days.

(21) Appl. No.: 09/380,967

(22) PCT Filed: Mar. 9, 1998

(86) PCT No.: PCT/EP98/01358

§ 371 Date: Sep. 14, 1999

§ 102(e) Date: Sep. 14, 1999

(87) PCT Pub. No.: WO98/41528

PCT Pub. Date: Sep. 24, 1998

(30) Foreign Application Priority Data

Mar. 15, 1997 (GB) .................................... 9705428

(51) Int. Cl.[7] ...................... A61K 31/426; C07D 513/02

(52) U.S. Cl. .......................... 514/370; 514/258; 514/333; 514/370; 544/281; 546/256; 548/154; 548/184; 548/190; 548/193

(58) Field of Search .................................. 514/258, 333, 514/370; 544/281; 546/256; 548/184, 190, 193, 154

(56) References Cited

U.S. PATENT DOCUMENTS

| | | | |
|---|---|---|---|
| 4,347,248 | 8/1982 | Wright, Jr. | 424/251 |
| 5,232,921 | * 8/1993 | Biziere et al. | 514/231.5 |
| 5,378,706 | 1/1995 | Biziere et al. | 514/232 |

FOREIGN PATENT DOCUMENTS

| | | |
|---|---|---|
| 600489 | 6/1994 | (EP) . |
| 683160 | 11/1995 | (EP) . |
| 97/02269 | 1/1997 | (WO) . |

OTHER PUBLICATIONS

Sharpe et al., *J. Med. Chem.*, 14(10), 1971, 977–982.

* cited by examiner

Primary Examiner—Mukund J. Shah
Assistant Examiner—Ben Schroeder
(74) Attorney, Agent, or Firm—Keil & Weinkauf

(57) ABSTRACT

Compounds of Formula I

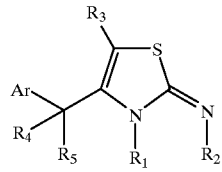

including pharmaceutically acceptable salts thereof in the form of individual enantiomers, racemates, or other mixtures of enantiomers, in which Ar is phenyl, naphthyl or benzo[b]thiophenyl, each of which may be optionally substituted; $R_1$ and $R_2$, which may be the same or different, independently are a) H, b) an alkyl group containing 1 to 6 carbon atoms, c) an alkenyl group containing 3 to 6 carbon atoms, d) a cycloalkyl group containing 3 to 7 carbon atoms, e) a cycloalkylmethyl group in which the ring contains 3 to 7 carbon atoms, f) an aryl or heteroaryl group optionally substituted g) an arylalkyl or heteroarylalkyl group each optionally substituted; or $R_1$ and $R_2$ form an alkylene chain optionally substituted by one or more alkyl groups each containing 1 to 3 carbon atoms, such that, together with the atoms to which they are attached, they form a 5 or 6 membered ring; $R_3$ is a) H, b) an aryl or heteroaryl group each optionally substituted c) an optionally substituted arylmethyl group; or d) an alkoxyalkyl group containing 3 to 6 carbon atoms; and $R_4$ and $R_5$, which may be the same or different, independently are an alkyl group containing 1 to 3 carbon atoms, or $R_4$ and $R_5$ together with the atom to which they are attached form a cycloalkyl ring containing 3 to 6 carbon atoms; processes to prepare such compounds; compositions containing such compounds and their use in the treatment of depression, anxiety, Parkinson's disease, obesity, cognitive disorders, seizures, neurological disorders and as neuroprotective agents; are described.

26 Claims, No Drawings

SUBSTITUTED 4-ARYLMETHYLENE-2-IMINO-2,3-DIHYDROTHIAZOLES AND DERIVATIVES AND THEIR PHARMACEUTICAL USE

The present invention relates to certain substituted 4-arylmethylene-2-imino-2,3-dihydrothiazoles which inhibit neuronal reuptake of 5-hydroxytryptamine and/or noradrenaline and/or dopamine, to processes for their preparation, to pharmaceutical compositions containing them and to their use in the treatment of depression, anxiety, Parkinson's disease, obesity, cognitive disorders, seizures, neurological disorders such as epilepsy, and as neuroprotective agents to protect against conditions such as stroke. The invention includes novel arylalkyl- and arylcycloalkyldihydroimidazo[2,1-b]thiazole, arylalkyl- and arylcycloalkyldihydro-5H-thiazolo[3,2-a]pyrimidine and arylalkyl- and arylcycloalkyldihydrothiazole compounds.

Sharpe C. J and Shadbolt R. S. disclose certain dihydroimidazo[2,1-b]thiazole compounds having antidepressant activity, Journal of Medicinal Chemistry, 1971, Vol 14 No.10, p977–982. However, the document also states that these compounds were generally less active and more toxic than the imidazolines also disclosed in the document. The compounds of the present invention are not disclosed or suggested in this document.

PCT/EP96/02676 discloses substituted benzo[b]thiophen-3-yldihydro-imidazo[2,1-b]thiazole, benzo[b]thiophen-3-yldihydro-5H-thiazolo[3,2-a]pyrimidine, benzo[b]furan-3-yldihydroimidazo[2,1-b]thiazole and benzo[b]furan-3-yldihydro-5H-thiazolo[3,2-a]pyrimidine compounds which have affinity for 5-$HT_{1A}$ receptors and which inhibit neuronal reuptake of 5-hydroxytryptamine and/or noradrenaline. These compounds are stated to be useful in the treatment of CNS disorders. The compounds of the present invention are not disclosed or suggested in this document.

EP683,160 discloses inter alia iminothiazoline compounds of Formula A

A

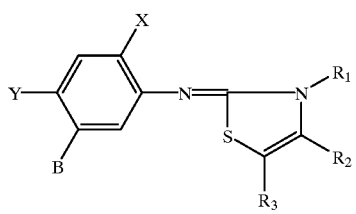

in which inter alia
R$_1$ is $C_1$–$C_6$ (halo)alkyl, R$_2$ is $C_1$–$C_6$ (halo)alkyl, $C_7$–$C_{17}$ aralkyl which may be substituted with one or more $C_1$–$C_3$ (halo)alkyl groups, $C_1$–$C_3$ (halo)alkoxy groups or halogen atoms, aryl which may be substituted; R$_3$ is hydrogen, $C_1$–$C_6$ (halo)alkyl or a group of the general formula: $CO_2R_6$; X is hydrogen, chlorine or fluorine; Y is chlorine, fluorine, bromine, nitro or cyano; R$_6$ is hydrogen or $C_1$–$C_3$ (halo)alkyl; B is nitro, or a group of the general formula: SR$_4$, or OR$_4$; R$_4$ is $C_1$–$C_6$ (halo) alkyl, $C_3$–$C_6$ (halo)alkenyl; wherein the term "(halo)" as used in the names of the above substituents means that they may be substituted with one or more halogen atoms; which are herbicides.

EP600,489 discloses a process for preparing compounds of Formula B

B

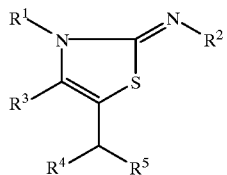

wherein R$^1$ is optionally substituted alkyl, optionally substituted cycloalkyl, optionally substituted aryl or optionally substituted heteroaryl; R$^2$ is hydrogen, optionally substituted alkyl, optionally substituted cycloalkyl, optionally substituted aryl, and R$^3$, R$^4$ and R$^5$ are the same or different, each of which is hydrogen, optionally substituted alkyl or optionally substituted aryl.

U.S. Pat. No. 4,347,248 discloses 2,3-disubstitutedthiazolo[3,2-a][1,3]diazacyclenes of Formula C

C

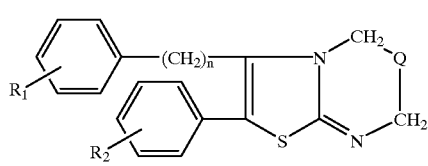

wherein R$_1$ is hydrogen, fluoro, chloro, bromo, alkyl having up to 3 carbon atoms or dimethylamino; R$_2$ is hydrogen, fluoro, chloro, bromo or alkyl having up to 3 carbon atoms; n is zero, one or two; and Q is a divalent moiety of the formula; —CH$_2$—, —C(CH$_3$)$_2$——CH$_2$CH$_2$— or —CH$_2$CH$_2$CH$_2$—; which are diuretics.

U.S. Pat. No. 4,325,955 discloses 3-benzhydrylthiazolo[3,2-a][1,3]diazacyclenes which are diuretics.

Certain cyclic 2-iminothiazoles are disclosed in J.Chem.Soc. 1995, 2943–2948 and J.Chem.Soc. Perkin Trans. 1, 1989, 643–648.

The present invention provides compounds of Formula I

I

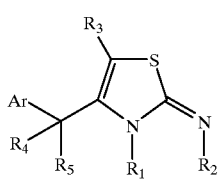

including pharmaceutically acceptable salts thereof in the form of individual enantiomers, racemates, or other mixtures of enantiomers,
in which:
Ar is phenyl, naphthyl or benzo[b]thiophenyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) a phenoxy group optionally substituted by one or more halo or f) phenyl optionally substituted by one or more halo;

R$_1$ and R$_2$, which may be the same or different, independently are a) H, b) an alkyl group containing 1 to 6 carbon atoms, c) an alkenyl group containing 3 to 6 carbon atoms, d) a cycloalkyl group containing 3 to 7 carbon atoms, e) a cycloalkylmethyl group in which the ring contains 3 to 7 carbon atoms, f) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo, g) an arylalkyl or heteroarylalkyl group in which the alkyl chain contains 1 to 3 carbon atoms and in which the aryl or heteroaryl group may optionally be substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo; or $R_1$ and $R_2$ form an alkylene chain optionally substituted by one or more alkyl groups each containing 1 to 3 carbon atoms, such that, together with the atoms to which they are attached, they form a 5 or 6 membered ring, $R_3$ is a) H, b) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo, c) an arylmethyl group in which the aryl is optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo; or d) an alkoxyalkyl group containing 3 to 6 carbon atoms; and $R_4$ and $R_5$, which may be the same or different, independently are an alkyl group containing 1 to 3 carbon atoms, or $R_4$ and $R_5$ together with the atom to which they are attached form a cycloalkyl ring containing 3 to 6 carbon atoms.

It will be understood that the term halo, when used herein, includes fluoro, chloro, bromo and iodo. It will be understood that in alkyl groups, alkylthio groups and alkoxy groups containing more than two carbon atoms the alkyl group may be straight or branched.

The term aryl as used herein means phenyl or naphthyl preferably phenyl. The term heteroaryl as used herein means aryl in which one or more of the ring carbon atoms is replaced by a heteroatom such as N, S or O and furyl and thienyl. Preferably heteroaryl means furyl, pyridyl or thienyl.

In preferred compounds of Formula I, Ar is naphthyl, benzo[b]thiophenyl or phenyl optionally substituted by one or more substituents selected from halo, an alkylthio group containing 1 to 3 carbon atoms, or a phenoxy group. In more preferred compounds, Ar is naphthyl, benzo[b]thiophenyl or phenyl optionally substituted by one or more substituents selected from chloro, bromo, methylthio, or phenoxy. Most preferably, Ar is 2-naphthyl, benzo[b]thiophen-2-yl, 4-chlorophenyl, 3,4-dichlorophenyl, 4-bromophenyl or 4-methylthiophenyl.

In preferred compounds of Formula I, $R_1$ and $R_2$, which may be the same or different, independently are a) H, b) an alkyl group containing 1 to 4 carbon atoms, c) an alkenyl group containing 3 or 4 carbon atoms, d) a cycloalkyl group containing 3 to 5 carbon atoms, e) a cycloalkylmethyl group in which the ring contains 3 to 5 carbon atoms, f) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms, g) an arylalkyl or heteroarylalkyl group in which the alkyl chain contains 1 or 2 carbon atoms and in which the aryl or heteroaryl group may optionally be substituted by one or more substituents selected from halo or an alkoxy group containing 1 to 3 carbon atoms; or $R_1$ and $R_2$ form an alkylene chain such that, together with the atoms to which they are attached, they form a 5 or 6 membered ring, optionally substituted by one or more methyl groups.

In more preferred compounds, $R_1$ and $R_2$ are a) an alkyl group containing 1 to 4 carbon atoms, b) allyl, c) cyclopentyl, d) cyclopropylmethyl, e) an aryl group optionally substituted by one or more substituents selected from i) halo, ii) methyl, iii) trifluoromethyl, iv) ethoxy, f) an arylalkyl or heteroarylalkyl group in which the alkyl chain contains 1 or 2 carbon atoms and in which the aryl or heteroaryl group may optionally be substituted by one or more substituents selected from halo or methoxy; or $R_1$ and $R_2$ form an alkylene chain such that, together with the atoms to which they are attached, they form a 5 or 6 membered ring, optionally substituted by one or more methyl groups.

Most preferably, $R_1$ and $R_2$ are methyl, ethyl, propyl, isopropyl, butyl, isobutyl, allyl, cyclopropylmethyl, benzyl, 4-fluorobenzyl, pyrid-3-ylmethyl, furfuryl, phenethyl or 2-(3,4-dimethoxyphenyl)ethyl; or $R_1$ and $R_2$ form an alkylene chain such that, together with the atoms to which they are attached, they form a 5 or 6 membered ring, optionally substituted by a methyl group.

In one group of especially preferred compounds of Formula I, $R_1$ and $R_2$ are identical and satisfy any of the above definitions. In another group of especially preferred compounds of Formula I, $R_1$ and $R_2$ form an alkylene chain such that, together with the atoms to which they are attached, they form a 5 or 6 membered ring, optionally substituted by a methyl group.

In preferred compounds of Formula I, $R_3$ is H, an aryl or heteroaryl group optionally substituted by one or more halo, an arylmethyl group in which the aryl is optionally substituted by one or more halo, or an alkoxyalkyl group containing 3 to 6 carbon atoms. In more preferred compounds $R_3$ is H, phenyl, 4-chlorophenyl, benzyl or 2-methoxyethyl. Most preferably, $R_3$ is H.

In preferred compounds of Formula I, $R_4$ and $R_5$, which may be the same or different, independently are methyl, or $R_4$ and $R_5$ together with the atom to which they are attached form a cycloalkyl ring containing 3 to 6 carbon atoms. Most preferably $R_4$ and $R_5$ are methyl, or $R_4$ and $R_5$ together with the atom to which they are attached form a cyclobutane, cyclopentane or cyclohexane ring.

A preferred group of compounds of Formula I is represented by Formula Ia

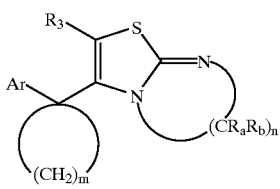

including pharmaceutically acceptable salts thereof in the form of individual enantiomers, racemates, or other mixtures of enantiomers,
in which
   m is 2, 3 or 4;
   n is 2 or 3;
   Ar is phenyl or naphthyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, or e) phenyl; and
   $R_a$ and $R_b$ independently are H or an alkyl group containing 1 to 3 carbon atoms optionally substituted by one or more halo; and
   $R_3$ is H.

In preferred compounds of Formula Ia, m is 3.
In preferred compounds of Formula Ia, n is 2.
In preferred compounds of Formula Ia, Ar is naphthyl, or phenyl substituted by one or two halo substituents. More preferably Ar is naphthyl, or phenyl substituted by one or two chloro substituents. Most preferably, Ar is 2-naphthyl or 4-chlorophenyl or 3,4-dichlorophenyl.
In preferred compounds of Formula Ia, $R_a$, $R_b$ and $R_3$ are each H.
In one group of preferred compounds of Formula Ia, m is 3; n is 2 or 3; Ar is phenyl or naphthyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, or e) phenyl; $R_a$ and $R_b$ independently are H or an alkyl group containing 1 to 3 carbon atoms optionally substituted by one or more halo and $R_3$ is H. Preferably, $R_a$, $R_b$ and $R_3$ are each H.
In a further group of preferred compounds of Formula Ia, m is 3; n is 2; Ar is phenyl or naphthyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, or e) phenyl; and $R_a$ and $R_b$ independently are H or an alkyl group containing 1 to 3 carbon atoms optionally substituted by one or more halo and $R_3$ is H. Preferably, $R_a$, $R_b$ and $R_3$ are each H.

Compounds of Formula I may exist as salts with pharmaceutically acceptable acids. The present invention includes all such salts. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid.

Certain compounds of Formula I may exist in different tautomeric forms or as different geometric isomers, and the present invention includes each tautomer and/or geometric isomer of compounds of Formula I and mixtures thereof.

Certain compounds of Formula I may exist in different stable conformational forms which may be separable. For example, if $R_3$ is a bulky group there may be restricted rotation about one or more single bond or bonds due to steric hindrance. Torsional asymmetry due to restricted rotation about an asymmetric single bond, for example because of steric hindrance or ring strain, may permit separation of different conformers. The present invention includes each conformational isomer of compounds of Formula I and mixtures thereof.

Certain compounds of Formula I and their salts may exist in more than one crystal form and the present invention includes each crystal form and mixtures thereof. Certain compounds of Formula I and their salts may also exist in the form of solvates, for example hydrates, and the present invention includes each solvate and mixtures thereof.

Certain compounds of Formula I contain one or more chiral centres, and exist in different optically active forms. When compounds of Formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of Formula I contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of Formula I and mixtures thereof.

Specific compounds of Formula I are
3-[1-(3,4-Dichlorophenyl)cyclobutyl]-5,6-dihydroimidazo [2,1-b]thiazole;
3-[1-(4-Chlorophenyl)cyclobutyl]-6,7-dihydro-5H-thiazolo [3,2-a]pynimidine;
3-[1-(4-Chlorophenyl)cyclobutyl]-5,6-dihydroimidazo[2,1-b]thiazole;
3-[1-(3,4-Dichlorophenyl)cyclobutyl]-6,7-dihydro-5H-thiazolo[3,2-a]pyrimidine;
3-[1-(2-Naphthyl)cyclobutyl]-5,6-dihydroimidazo[2,1-b] thiazole;
3-[1-(3,4-Dichlorophenyl)cyclopentyl]-5,6-dihydroimidazo [2,1-b]thiazole;
2-Benzyl-3-[1-(4-chlorophenyl)cyclobutyl]-5,6-dihydroimidazo[2,1-b]thiazole;

3-[1-(3,4-Dichlorophenyl)cyclobutyl]-2-(2-methoxyethyl)-5,6-dihydroimidazo[2,1-b]thiazole;

3-[1-(3,4-Dichlorophenyl)cyclobutyl]-2-phenyl-5,6-dihydroimidazo[2,1-b]thiazole;

2-(4-Chlorophenyl)-3-[1-(3,4-dichlorophenyl)cyclobutyl]-5,6-dihydroimidazo[2,1-b]thiazole;

3-[1-(3,4-Dichlorophenyl)-1-methylethyl]-5,6-dihydroimidazo[2,1-b]thiazole;

3-[1-(Benzo[b]thiophen-2-yl)cyclobutyl]-5,6-dihydroimidazo[2,1-b]thiazole;

3-[1-(3,4-Dichlorophenyl)cyclobutyl]-5-methyl-5,6-dihydroimidazo[2,1-b]thiazole;

3-[1-(3,4-Dichlorophenyl)cyclobutyl]-6-methyl-5,6-dihydroimidazo[2,1-b]thiazole;

4-[1-(3,4-Dichlorophenyl)cyclobutyl]-3-methyl-2-methylimino-2,3-dihydrothiazole;

4-[1-(3,4-Dichlorophenyl)cyclobutyl]-3-ethyl-2-ethylimino-2,3-dihydrothiazole;

4-[1-(3,4-Dichlorophenyl)cyclobutyl]-3-propyl-2-propylimino-2,3-dihydrothiazole;

4-[1-(3,4-Dichlorophenyl)cyclobutyl]-3-isopropyl-2-isopropylimino-2,3-dihydrothiazole;

3-Butyl-2-butylimino-4-[1-(3,4-dichlorophenyl)cyclobutyl]-2,3-dihydrothiazole;

4-[1-(3,4-Dichloropheny)cyclobutyl]-3-isobutyl-2-isobutylimino-2,3-dihydrothiazole;

3-Allyl-2-allylimino-4-[1-(3,4-dichlorophenyl)cyclobutyl]-2,3-dihydrothiazole;

4-[1-(3,4-Dichlorophenyl)cyclobutyl]-3-cyclopropylmethyl-2-cyclopropylmethylimino-2,3-dihydrothiazole;

3-Benzyl-2-benzylimino-4-[1-(3,4-dichlorophenyl)cyclobutyl]-2,3-dihydrothiazole;

4-[1-(3,4-Dichlorophenyl)cyclobutyl]-3-(4-fluorobenzyl)-2-(4-fluorobenzylimino)-2,3-dihydrothiazole;

4-[1-(3,4-Dichlorophenyl)cyclobutyl]-3-phenethyl-2-phenethylimino-2,3-dihydrothiazole;

4-[1-(3,4-Dichlorophenyl)cyclobutyl]-3-(3-pyridylmethyl)-2-(3-pyridylmethylimino)-2,3-dihydrothiazole;

4-[1-(3,4-Dichlorophenyl)cyclobutyl]-3-furfuryl-2-furfurylimino-2,3-dihydrothiazole;

4-[1-(3,4-Dichlorophenyl)cyclobutyl]-3-phenyl-2-phenylimino-2,3-dihydrothiazole;

4-[1-(3,4-Dichlorophenyl)cyclobutyl]-3-(p-tolyl)-2-(p-tolylimino)-2,3-dihydrothiazole;

4-[1-(3,4-Dichlorophenyl)cyclobutyl]-3-(otolyl)-2-(o-tolylimino)-2,3-dihydrothiazole;

4-[1-(3,4-Dichlorophenyl)cyclobutyl]-3-(3-trifluoromethylphenyl)-2-(3-trifluoromethylphenylimino)-2,3-dihydrothiazole;

4-[1-(3,4-Dichlorophenyl)cyclobutyl]-3-(2,4-xylyl)-2-(2,4-xylylimino)-2,3-dihydrothiazole;

4-[1-(3,4-Dichlorophenyl)cyclobutyl]-3-(4-ethoxyphenyl)-2-(4-ethoxyphenylimino)-2,3-dihydrothiazole;

4-[1-(3,4-Dichlorophenyl)cyclobutyl]-3-(3,4-dimethoxyphenethyl)-2-(3,4-dimethoxyphenethylimino)-2,3-dihydrothiazole;

3-[1-(2-Naphthyl)cyclobutyl]-6,7-dihydro-5H-thiazolo[3,2-a]pyrimidine;

5-Methyl-3-[1-(2-naphthyl)cyclobutyl]-5,6-dihydroimidazo[2,1-b]thiazole;

6-Methyl-3-[1-(2-naphthyl)cyclobutyl]-5,6-dihydroimidazo[2,1-b]thiazole;

3-Methyl-2-methylimino-4-[1-(2-naphthyl)cyclobutyl]-2,3-dihydrothiazole;

3-Ethyl-2-ethylimino-4-[1-(2-naphthyl)cyclobutyl]-2,3-dihydrothiazole;

4-[1-(2-Naphthyl)cyclobutyl]-3-propyl-2-propylimino-2,3-dihydrothiazole;

3-Isopropyl-2-isopropylimino-4-[1-(2-naphthyl)cyclobutyl]-2,3-dihydrothiazole;

3-Butyl-2-butylimino-4-[1-(2-naphthyl)cyclobutyl]-2,3-dihydrothiazole;

3-Isobutyl-2-isobutylimino-4-[1-(2-naphthyl)cyclobutyl]-2,3-dihydrothiazole;

3-Allyl-2-allylimino-4-[1-(2-naphthyl)cyclobutyl]-2,3-dihydrothiazole;

3-Cyclopropylmethyl-2-cyclopropylmethylimino-4-[1-(2-naphthyl)cyclobutyl]-2,3-dihydrothiazole;

3-Benzyl-2-benzylimino-4-[1-(2-naphthyl)cyclobutyl]-2,3-dihydrothiazole;

3-(4-Fluorobenzyl)-2-(4-fluorobenzylimino)-4-[1-(2-naphthyl)cyclobutyl]-2,3-dihydrothiazole;

4-[1-(2-Naphthyl)cyclobutyl]-3-phenethyl-2-phenethylimino-2,3-dihydrothiazole hydrobromide;

4-[1-(2-Naphthyl)cyclobutyl]-3-(3-pyridylmethyl)-2-(3-pyridylmethylimino)-2,3-dihydrothiazole;

3-Furfuryl-2-furfurylimino-4-[1-(2-naphthyl)cyclobutyl]-2,3-dihydrothiazole;

4-[1-(2-Naphthyl)cyclobutyl]-3-phenyl-2-phenylimino-2,3-dihydrothiazole;

4-[1-(2-Naphthyl)cyclobutyl]-3-(p-tolyl)-2-(p-tolylimino)-2,3-dihydrothiazole;

4-[1-(2-Naphthyl)cyclobutyl]-3-(o-tolyl)-2-(o-tolylimino)-2,3-dihydrothiazole;

4-[1-(2-Naphthyl)cyclobutyl]-3-(2,4-xylyl)-2-(2,4-xylylimino)-2,3-dihydrothiazole;

3-Cyclopentyl-2-cyclopentylimino-4-[1-(2-naphthyl)cyclobutyl]-2,3-dihydrothiazole;

3-(4-Ethoxyphenyl)-2-(4-ethoxyphenylimino)-4-[1-(2-naphthyl)cyclobutyl]-2,3-dihydrothiazole;

3-(3,4-Dimethoxyphenethyl)-2-(3,4-dimethoxyphenethylimino)-4-[1-(2-naphthyl)cyclobutyl]-2,3-dihydrothiazole;

3-Butyl-2-butylimino-4-[1-(4-chlorophenyl)cyclobutyl]-2,3-dihydrothiazole;

4-[1-(4-Bromophenyl)cyclobutyl]-3-butyl-2-butylimino-2,3-dihydrothiazole;

3-Butyl-2-butylimino-4-[1-(4-methylthiophenyl)cyclobutyl]-2,3-dihydrothiazole;

3-Butyl-2-butylimino-4-[1-(4-phenoxyphenyl)cyclobutyl]-2,3-dihydrothiazole;

3-Butyl-2-butylimino-4-[1-(4-chlorophenyl)cyclopentyl]-2,3-dihydrothiazole;

3-Butyl-2-butylimino-4-(1-phenylcyclohexyl)-2,3-dihydrothiazole;

3-Butyl-2-butylimino-4-[1-(4-chlorophenyl)-1-methylethyl]-2,3-dihydrothiazole;

3-Butyl-2-butylimino-4-[1-(3,4-dichlorophenyl)-1-methylethyl]-2,3-dihydrothiazole;

4-[1-(4-Chlorophenyl)cyclobutyl-3-phenethyl-2-phenethylimino-2,3-dihydrothiazole;

4-[1-(4-Chlorophenyl)cyclobutyl]-3-(3,4-dimethoxyphenethyl)-2-(3,4-dimethoxyphenethylimino)-2,3-dihydrothiazole;

4-[1-(4-Bromophenyl)cyclobutyl]-3-(3,4-dimethoxyphenethyl)-2-(3,4-dimethoxyphenethylimino)-2,3-dihydrothiazole;

4-[1-(4-Chlorophenyl)cyclopentyl]-3-(3,4-dimethoxyphenethyl)-2-(3,4-dimethoxyphenethylimino)-2,3-dihydrothiazole;

3-(3,4-Dimethoxyphenethyl)-2-(3,4-dimethoxyphenethylimino)-4-(1-phenylcyclohexyl)-2,3-dihydrothiazole;

4-[1-(3,4-Dichlorophenyl)-1-methylethyl]-3-(3,4-dimethoxyphenethyl)-2-(3,4-dimethoxyphenethylimino)-2,3-dihydrothiazole;
3-[1-(4-Bromophenyl)cyclobutyl]-5,6-dihydroimidazo[2,1-b]thiazole;
3-[1-(4-Chlorophenyl)cyclopentyl]-5,6-dihydroimidazo[2,1-b]thiazole;
3-(1-Phenylcyclohexyl)-5,6-dihydroimidazo[2,1-b]thiazole;
3-[1-(4-Chlorophenyl)-1-methylethyl]-5,6-dihydroimidazo[2,1-b]thiazole;
3-[1-(3,4-Dichlorophenyl)-1-methylethyl]-5,6-dihydroimidazo[2,1-b]thiazole;
3-[1-(3-Fluorophenyl)cyclobutyl]-5,6-dihydroimidazo[2,1-b]thiazole;
3-[1-(4-Methylthiophenyl)cyclobutyl]-5,6-dihydroimidazo[2,1-b]thiazole;
including pharmaceutically acceptable salts thereof and individual enantiomers, racemates or other mixtures of enantiomers.

The present invention also includes pharmaceutical compositions comprising a therapeutically effective amount of a compound of Formula I or a salt thereof together with a pharmaceutically acceptable diluent or carrier.

As used hereinafter, the term "active compound" denotes a compound of Formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacists art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Solid oral dosage forms may be formulated in a manner known to those skilled in the art so as to give a sustained release of the active compound. Enteric coated, solid oral dosage forms comprising compositions of the present invention may be advantageous, depending on the nature of the active compound. Various materials, for example shellac and/or sugar, may be present as coatings, or to otherwise modify the physical form of the oral dosage form. For example tablets or pills may, if desired, be provided with enteric coatings by known methods, for example by the use of cellulose acetate phthalate and/or hydroxy propyl methylcellulose phthalate.

Capsules and/or caplets (for example hard or soft gelatin capsules) comprising the active compound (with or without added excipients such as a fatty oil), may be prepared by conventional means and, if desired, provided with enteric coatings in a known manner. The contents of the capsule and/or caplet may be formulated using known methods to give sustained release of the active compound.

Liquid oral dosage forms comprising compositions of the present invention may be an elixir, suspension and/or syrup (for example, aqueous suspensions containing the active compound in an aqueous medium in the presence of a non-toxic suspending agent [such as sodium carboxymethylcellulose] and/or oily suspensions containing the active compound in a suitable vegetable oil [such as arachis oil and/or sunflower oil]). Liquid oral dosage forms may also comprise one or more sweetening agent, flavouring agent, preservatives and/or mixtures thereof.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Preferably each of the above oral dosage forms may contain from about 1 mg to about 1000 mg, more preferably from about 5 mg to about 500 mg (for example 10 mg, 50 mg, 100 mg, 200 mg, or 400 mg) of the active compound.

Compositions of the invention suitable for rectal administration are the known pharmaceutical forms for such administration, for example, suppositories with hard fat, semi-synthetic glyceride, cocoa butter and/or polyethylene glycol bases.

Pharmaceutical compositions may also be administered parenterally (for example subcutaneously, intramuscularly, intradermally and/or intravenously [such as by injection and/or infusion] in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthethetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises a compound of Formula I for use as a medicament.

The pharmaceutical compositions containing a therapeutically effective amount of a compound of Formula I may be used to treat depression, anxiety, Parkinson's disease, obesity, cognitive disorders, seizures, neurological disorders such as epilepsy, and as neuroprotective agents to protect against conditions such as stroke in human beings. Whilst the precise amount of active compound administered in such treatment will depend on a number of factors, for example the age of the patient, the severity of the condition and the past medical history, and always lies within the sound discretion of the administering physician, the amount of active compound administered per day is in the range 1 to 1000 mg preferably 5 to 500 mg given in single or divided doses at one or more times during the day.

In yet another aspect, the present invention provides the use of a compound of Formula I in the manufacture of a medicament for use in the treatment of depression, anxiety, Parkinson's disease, obesity, cognitive disorders, seizures, neurological disorders such as epilepsy, and as a neuroprotective agent to protect against conditions such as stroke.

The present invention also provides a method of treating depression, anxiety, Parkinson's disease, obesity, cognitive disorders, seizures, neurological disorders such as epilepsy, and of neuroprotection to protect against conditions such as stroke in human beings which comprises the administration of a therapeutically effective amount of a compound of Formula I to a patient in need thereof.

Compounds of Formula I may be administered as a method of treating Parkinson's Disease either alone or in combination with a dopamine precursor, such as levodopa and/or a dopa decarboxylase inhibitor such as carbidopa or benserazide, or in combination with a dopamine agonist such as pramipexole or in combination with catechol-O-methyltransferase inhibitors such as tolcapone or entacapone.

Processes for the preparation of compounds of Formula I will now be described. The processes may be performed on an individual basis, or by multiple parallel synthesis, also known as High Speed Analoguing. The processes are preferably carried out at atmospheric pressure.

Compounds of Formula I may be prepared by heating a compound of Formula II

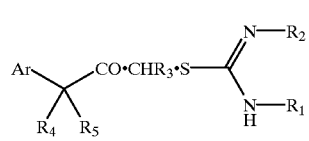

II in which Ar, $R_1$, $R_2$, $R_3$, $R_4$ and $R_5$ are as hereinbefore defined, optionally in the presence of an acid, for example acetic acid, at a temperature in the range 0–200° C.; preferably in the range 20–150° C.

Compounds of Formula II may be prepared by reaction of a compound of Formula III

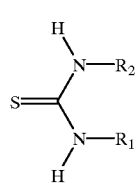

III in which $R_1$ and $R_2$ are as hereinbefore defined, with a compound of Formula IV

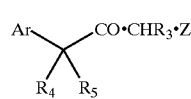

IV in which Z is a leaving group, for example a halo such as bromo, and Ar, $R_3$, $R_4$ and $R_5$ are as hereinbefore defined, at a temperature in the range 0–200° C., in the presence of a solvent, for example acetone; preferably by heating at a temperature in the range 20–150° C.

Compounds of Formula I may also be prepared directly by reaction of a compound of Formula III with a compound of Formula IV at a temperature in the range of 0–200° C., optionally in the presence of an acid, for example acetic acid, and optionally in the presence of a solvent, for example ethanol, without isolation of the intermediate of Formula II; preferably by heating at a temperature in the range 20–150° C.

Compounds of Formula IV in which Z is halo may be prepared by reaction of a compound of Formula V

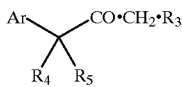

V in which Ar, $R_3$, $R_4$ and $R_5$ are as hereinbefore defined, with a halogenating agent, for example bromine at a temperature in the range 0–200° C. in the presence of a solvent, for example ether or methanol and dichloromethane; preferably at an initial temperature of 0–50° C., then at a temperature in the range 20–150° C.

Compounds of Formula V may be readily prepared by methods described in, or closely analogous to those described in the patent GB2098602.

Compounds of Formula Ia may be prepared by processes analogous to those described for the preparation of compounds of Formula I.

The ability of compounds of Formula I to interact with dopamine (DA) reuptake sites has been demonstrated for the products of Examples 1 to 5 by the following test which determines the ability of compounds to inhibit dopamine uptake in vitro.

Striatal tissue from the brains of male Charles River rats weighing 150–250 g was homogenised in ice-cold 0.32M sucrose (1:10 w/v) using a motor driven teflon pestle (difference in diameter between mortar and pestle 0.5 mm). Nuclei and cell debris were removed by centrifugation at 1,500 g at 4° C. for 10 minutes. The pellet (P1) was discarded and the supernatant centrifuged at 28,000 g at 4° C. for 10 minutes. The crude synaptosomal pellet (P2) was resuspended in Krebs-Henseleit buffer (equivalent to 4.2 mg wet weight of tissue/ml).

Crude synaptosomes were incubated in a shaking water bath at 37° C. for 15 minutes. Aliquots (150 μl; equivalent to 0.625 mg wet weight of tissue/tube) were then added to tubes containing 275 μl of Krebs-Henseleit buffer and 50 μl of Krebs-Henseleit buffer (total uptake) or 50 μl of test compound (10 concentrations ranging from $10^{-11}$–$10^{-4}$M or 50 μl of GBR 12909 ($10^{-5}$M; non-specific uptake). Uptake was initiated by the addition of 25 μl of freshly prepared [$^3$H]dopamine (2.5 nM), followed by vortexing and was continued for 5 minutes at 37° C. in the shaking water bath.

Uptake was terminated by filtration under vacuum through Skatron 11735 filters using a Skatron cell harvester. Filters were then washed with 8 ml ice-cold saline. The scored filter paper discs were punched into vials, scintillation fluid added and radioactivity determined by liquid scintillation counting.

The ability of compounds of Formula I to interact with 5-hydroxytryptamine (5-HT) reuptake sites has been demonstrated for the products of Examples 1 to 5 by the following test which determines the ability of compounds to inhibit 5-HT uptake in vitro.

Frontal cortical tissue from the brains of male Sprague-Dawley rats (Charles River; weight range 150–250 g) was homogenised in ice-cold 0.32M sucrose (1:10 w/v) using a motor driven teflon pestle (difference in diameter between mortar and pestle 0.5 mm). Nuclei and cell debris were removed by centrifugation at 1,500 g at 4° C. for 10 minutes. The pellet (P1) was discarded and the supernatant centrifuged at 28,000 g at 4° C. for 10 minutes. The crude synaptosomal pellet (P2) was resuspended in Krebs-Henseleit buffer (equivalent to 8.3 mg wet weight of tissue/ml).

Crude synaptosomes were incubated in a shaking water bath at 37° C. for 15 minutes. Aliquots (150 μl; equivalent to 1.25 mg wet weight of tissue/tube) were then added to tubes containing 275 μl of Krebs-Henseleit buffer and 50 μl of Krebs-Henseleit buffer (total uptake) or 50 μl of test compound (at 10 concentrations ranging from $10^{-11}$–$10^{-4}$M) or 50 μl of zimeldine ($10^{-5}$M; non-specific uptake). Uptake was initiated by the addition of 25 μl of freshly prepared [$^3$H]5-HT (2 nM), followed by vortexing, and was continued for 5 minutes at 37° C. in the shaking water bath. Uptake was terminated by filtration under vacuum through Skatron 11734 filters using a Skatron cell harvester. Filters were then washed with 8 ml ice-cold saline. The scored filter paper discs were punched into vials, scintillation fluid added and radioactivity determined by liquid scintillation counting.

The ability of compounds of Formula I to interact with noradrenaline (NA) reuptake sites has been demonstrated for the products of Examples 1 to 5 by the following test which determines the ability of compounds to inhibit noradrenaline uptake in vitro.

Frontal cortical tissue from the brains of male Sprague-Dawley rats (Charles River; weight range 150–250 g) was homogenised in ice-cold 0.32M sucrose (1:10 w/v) using a motor driven teflon pestle (difference in diameter between mortar and pestle 0.5 mm). Nuclei and cell debris were removed by centrifugation at 1,500 g at 4° C. for 10 minutes. The pellet (P1) was discarded and the supernatant centrifuged at 28,000 g at 4° C. for 10 minutes. The crude synaptosomal pellet (P2) was resuspended in Krebs-Physiological buffer (equivalent to 16.7 mg wet weight of tissue/ml).

Crude synaptosomes were incubated in a shaking water bath at 37° C. for 15 minutes. Aliquots (150 μl; equivalent to 2.5 mg wet weight of tissue/tube) were then added to tubes containing 275 μl of Krebs-Physiological buffer and 50 μl of Krebs-Physiological buffer (total uptake) or 50 μl of test compound (at 10 concentrations ranging from $10^{-7}$–$10^{-4}$M) or 50 μl of desipramine ($10^{-5}$M; non-specific uptake). Uptake was initiated by the addition of 25 μl of freshly prepared [$^3$H]noradrenaline (10 nM), followed by vortexing and was continued for 5 minutes at 37° C. in the shaking water bath. Uptake was terminated by filtration under vacuum through Whatman GF/B filters using a Brandel cell harvester. Filters were then washed with 8 ml ice-cold saline. The scored filter paper discs were placed into vials, scintillation fluid added and radioactivity determined by liquid scintillation counting.

For each of the dopamine (DA) uptake, 5-hydroxytryptamine (5-HT) uptake and noradrenaline (NA) uptake inhibition tests, the percentage inhibition of specific uptake of the tritiated ligand was calculated for each concentration of test compound. Inhibition curves were then produced. The concentration which gave 50% inhibition of specific uptake ($IC_{50}$) was obtained from the curve. The inhibition constant ($K_i$) was then calculated using the formula $$K_i = \frac{IC_{50}}{1 + ([\text{ligand}]/Km)}$$

in which [ligand] is the concentration of tritiated ligand used and Km is the affinity of the uptake site for the ligand. The $K_i$ values (nM) obtained in the above tests for DA, 5-HT and NA uptake inhibition for each of the final products of Examples 1 to 5 hereinafter are given in Table 1 below. Values are means of three independent determinations unless otherwise indicated.

TABLE 1

| Example No. | DA uptake | 5-HT uptake | NA uptake |
| --- | --- | --- | --- |
| 1 | 9.2 nM | 120 nM | 34 nM |
| 2 | 104 nM | 782 nM | 261 nM |
| 3 | 79 nM | 795 nM | 22 nM |
| 4 | 9.5 nM | 137 nM | 15 nM |
| 5 | 5.9 nM | 25 nM | 4.4 nM |

The ability of compounds of Formula I to interact with dopamine (DA) reuptake sites has been demonstrated for the products of Examples 6 to 76 by the following test which determines the ability of compounds to displace the standard ligand, [$^3$H]GBR 12935, from dopamine reuptake sites in vitro.

Striatal tissue from the brains of male Charles River rats weighing 150–250 g was homogenised in ice-cold 0.32M sucrose (1:80 w/v) using a motor driven teflon pestle (12 strokes, 800 rpm) and centrifuged at 1000 g for 12 minutes. The supernatant was stored on ice and the pellet was resuspended in 0.32M sucrose (1:80 w/v) and centrifuged at 850 g for 10 minutes. Combined supernatants were diluted to 1:320 w/v with ice-cold 50 mM Tris-HCl, pH 7.4 (at 25° C.) containing 200 mM sodium chloride and 5 mM potassium chloride (Tris buffer) and centrifuged at 40,000 g for 10 minutes. The resulting pellet was resuspended in 10 ml of 50 mM Tris buffer, incubated at 37° C. for 10 min, diluted in 50 mM Tris buffer (1:320 w/v) and recentrifuged at 40,000 g for 10 minutes. The final pellet was resuspended in 50 mM Tris buffer (equivalent to 1.25 mg wet weight of tissue/ml) and used immediately in the binding assay. All centrifugations were carried out at 4° C.

Membranes (800 μl; equivalent to 1 mg wet weight of tissue/tube) were incubated with 100 μl [$^3$H]GBR 12935 at a single concentration of 1 nM and 100 μl of distilled water (total binding) or 100 μl of test compound ($10^{-6}$M) or 100 μl of mazindol (1 μM; non-specific binding) for 90 min at 4° C.

Membrane bound radioactivity was recovered by filtration under vacuum through Whatman GF/C filters, pre-soaked for 1 h in 0.5% polyethylenimine, using a Brandel cell harvester. Filters were rapidly washed with 16 ml of ice-cold 50 mM Tris-HCl, pH 7.4 and radioactivity determined by liquid scintillation counting (2 ml Packard MV Gold scintillator).

The ability of compounds of Formula I to interact with 5-hydroxytryptamine (5-HT) reuptake sites has been demonstrated for the products of Examples 6 to 76 by the following test which determines the ability of compounds to displace the standard ligand, [$^3$H]paroxetine, from 5-HT reuptake sites in vitro.

Frontal cortical tissue from the brains of male Charles River rats weighing 150–250 g was homogenised in ice-cold 0.25M sucrose (1:30 w/v) using a Kinematic polytron (speed setting 6 for 30 seconds) and centrifuged at 1000 g for 12 minutes. The supernatant was stored on ice and the pellet was resuspended in 0.25M sucrose (1:20 w/v) and centrifuged at 850 g for 10 minutes. Combined supernatants were diluted to 1:100 w/v with ice-cold 50 mM Tris-HCl, pH 7.5 (at 25° C.) containing 120 mM sodium chloride and 5 mM potassium chloride (Tris buffer) and centrifuged at 40,000 g for 10 minutes. The resulting pellet was resuspended in 50 mM Tris buffer (1:100 w/v) and recentrifuged at 40,000 g for 10 minutes. The final pellet was resuspended in 50 mM Tris buffer (equivalent to 2 mg wet weight of tissue/ml) and used immediately in the binding assay. All centrifugations were carried out at 4° C.

Membranes (1000 μl; equivalent to 2 mg wet weight of tissue/tube) were incubated with 200 μl [$^3$H]paroxetine at a single concentration of 30 pM and 200 μl of distilled water (total binding) or 200 μl of test compound ($10^{-6}$M) or 200 μl of citalopram (1 μM; non-specific binding) for 2 h at 22° C.

Membrane bound radioactivity was recovered by filtration under vacuum through Whatman GFIC filters using a Brandel cell harvester. Filters were rapidly washed with 16 ml ice-cold 50 mM Tris buffer and radioactivity determined by liquid scintillation counting (2 ml Packard MV Gold scintillator).

The ability of compounds of Formula I to interact with noradrenaline (NA) reuptake sites has been demonstrated for the products of Examples 6 to 76 by the following test which determines the ability of compounds to displace the standard ligand, [$^3$H]nisoxetine, from noradrenaline reuptake sites in vitro.

Frontal cortical tissue from the brains of male Charles River rats weighing 150–250 g was homogenised in ice-cold 50 mM Tris-HCl, pH 7.4 (at 25° C.) containing 120 mM sodium chloride and 5 mM potassium chloride (Tris buffer; 1:60 w/v) using a Kinematic polytron (speed setting 6 for 30 seconds) and centrifuged at 40,000 g for 10 minutes. The supernatant was discarded and the pellet rehomogenised in Tris buffer, 1:60 w/v, and centrifuged at 40,000 g for 10 minutes. This step was repeated twice more so that, in total, the brain tissue was homogenised and centrifuged four times. The final pellet was resuspended in 50 mM Tris-HCl, pH 7.4 containing 300 mM sodium chloride and 5 mM potassium chloride (equivalent to 25 mg wet weight of tissue/ml) and used immediately in the binding assay. All centrifugations were performed at 4° C.

Membranes (400 μl; equivalent to 10 mg wet weight of tissue/tube) were incubated with 50 μl [$^3$H]nisoxetine at a single concentration of 0.6 nM and 50 μl of distilled water (total binding) or 50 μl of test compound ($10^{-6}$M) or 50 μl of mazindol (1 μM; non-specific binding) for 4 h at 4° C.

Membrane bound radioactivity was recovered by filtration under vacuum through Skatron 11734 filters using a Skatron cell harvester. Filters were rapidly washed with ice-cold 50 mM Tris-HCl, pH 7.4 containing 120 mM sodium chloride and 5 mM potassium chloride (wash setting 9,9,0) and radioactivity determined by liquid scintillation counting (1 ml Packard MV Gold scintillator).

For each of these tests measuring the ability of compounds of Formula I to displace standard ligands from dopamine (DA), 5-hydroxytryptamine (5-HT) and noradrenaline (NA) reuptake sites in vitro, the percentage displacement of specific binding of tritiated ligand by $10^{-6}$M test compound was calculated in the following way:

Firstly, specific binding of tritiated ligand in the absence (A) and presence (B) of test compound was determined:

In the absence of compound:

$$A \text{ (dpm)} = \text{Total binding (dpm)} - \text{Non-specific binding (dpm)}$$

In the presence of compound ($10^{-6}$M):

$$B \text{ (dpm)} = \text{Binding at } 10^{-6}\text{M (dpm)} - \text{Non-specific binding (dpm)}$$

The specific binding of tritiated ligand in the presence (B) of compound was then converted to a percentage of specific binding of tritiated ligand in the absence (A) of compound:

$$\% \text{ Specific binding at } 10^{-6}\text{M} = B \text{ (dpm)}/A\text{(dpm)} \times 100$$

The percentage displacement of specific binding of trtiated ligand by the test compound ($10^{-6}$M) was then obtained by subtraction of the percentage specific binding in the presence of compound from the percentage specific binding in the absence of compound, which is taken as the maximum binding and so equals 100%:

% Displacement at $10^{-6}$M=100−% Specific binding at $10^{-6}$M.

The values given below in Table 2 for examples 6 to 76 are % displacement of specific binding of tritiated ligand by $10^{-6}$M test compound and represent results from one test only. IA refers to <50% displacement.

TABLE 2

| Example No. | DA uptake | 5-HT uptake | NA uptake |
| --- | --- | --- | --- |
| 6 | 112% | 86% | 101% |
| 7 | 69% | 85% | IA |
| 8 | IA | 62% | IA |
| 9 | 60% | 75% | IA |
| 10 | 85% | 57% | IA |
| 11 | 102% | 57% | IA |
| 12 | 121% | 77% | 95% |
| 13 | 104% | 92% | 92% |
| 14 | 103% | 96% | 80% |
| 15 | 115% | 102% | 99% |
| 16 | 116% | 102% | 56% |
| 17 | 112% | 95% | 63% |
| 18 | 106% | 95% | 63% |
| 19 | 107% | 89% | IA |
| 20 | 105% | 104% | 91% |
| 21 | 108% | 103% | 50% |
| 22 | 79% | IA | IA |
| 23 | 83% | IA | IA |
| 24 | 90% | IA | IA |
| 25 | 108% | 95% | 66% |
| 26 | 116% | 92% | IA |
| 27 | 84% | IA | IA |
| 28 | 71% | IA | IA |
| 29 | 74% | IA | IA |
| 30 | 79% | IA | IA |
| 31 | 63% | IA | IA |
| 32 | 69% | IA | IA |
| 33 | 99% | 63% | IA |
| 34 | 109% | 100% | 110% |
| 35 | 109% | 99% | 107% |
| 36 | 108% | 101% | 101% |
| 37 | 110% | 101% | 102% |
| 38 | 111% | 102% | 95% |
| 39 | 108% | 100% | 58% |
| 40 | 113% | 97% | IA |
| 41 | 107% | 98% | 79% |
| 42 | 113% | 101% | 93% |
| 43 | 113% | 101% | 93% |
| 44 | 96% | 72% | IA |
| 45 | 96% | 59% | IA |
| 46 | 98% | 51% | IA |
| 47 | 109% | 99% | 92% |
| 48 | 101% | 94% | IA |
| 49 | 69% | 56% | IA |
| 50 | 68% | IA | IA |
| 51 | 69% | 54% | IA |
| 52 | 74% | IA | IA |
| 53 | 80% | 71% | IA |
| 54 | 69% | IA | IA |
| 55 | 91% | IA | IA |
| 56 | 93% | IA | IA |
| 57 | 94% | IA | IA |
| 58 | 92% | IA | IA |
| 59 | 73% | IA | IA |
| 60 | 106% | IA | IA |
| 61 | 68% | IA | IA |
| 62 | 55% | IA | IA |
| 63 | 107% | 52% | IA |
| 64 | 102% | IA | IA |
| 65 | 54% | IA | IA |
| 66 | 58% | IA | IA |

TABLE 2-continued

| Example No. | DA uptake | 5-HT uptake | NA uptake |
| --- | --- | --- | --- |
| 67 | 88% | IA | IA |
| 68 | 65% | IA | IA |
| 69 | 58% | IA | IA |
| 70 | 80% | IA | 52% |
| 71 | 96% | IA | 76% |
| 72 | 70% | IA | IA |
| 73 | 59% | IA | IA |
| 74 | 97% | 52% | IA |
| 75 | IA | 53% | IA |
| 76 | IA | 81% | IA |

The types of activity shown in Tables 1 and 2 are indicative of compounds having utility in the treatment of the stated indications, particularly Parkinson's disease. Compounds of Formula I may have an improved pharmacological profile over compounds known in the art.

The invention is illustrated by the following Examples which are given by way of example only. The final product of each of these Examples was characterised by one or more of the following procedures: high performance liquid chromatography; elemental analysis, nuclear magnetic resonance spectroscopy, mass spectroscopy and infrared spectroscopy.

EXAMPLE 1

Methylmagnesium iodide was prepared under nitrogen by dropwise addition of a solution of iodomethane (93.8 g) in ether (100 ml) to a stirred suspension of magnesium turnings (15.9 g) in ether (100 ml) initially at ambient temperature then, when the exothermic reaction commenced, at reflux temperature. After the addition was complete the mixture was stirred for 30 minutes, then a solution of 1-(3,4-dichlorophenyl)cyclobutanecarbonitrile (100 g) in ether (80 ml) was added dropwise at ambient temperature. The mixture was stirred at reflux temperature for 3 hours and at ambient temperature for 16 hours. The resulting solid was collected by filtration, washed well with ether, then added in portions to an ice-cold mixture of water (400 ml) and concentrated hydrochloric acid (250 ml). The resulting mixture was heated at 95° C. for 1 hour with occasional stirring then cooled to ambient temperature. The product was extracted into ether (6×150 ml), the extracts were dried (MgSO$_4$), and the solvent was removed in vacuo. The residue was distilled to give 1-[1-(3,4-dichlorophenyl) cyclobutyl]ethanone as a pale yellow oil (89.6 g), b.p. 116–118° C./0.13 mbar.

A solution of bromine (10.2 ml) in dichloromethane (50 ml) was added dropwise over 3.5 hours at 10–15° C. under nitrogen to a stirred solution of 1-[1-(3,4-dichlorophenyl) cyclobutyl]ethanone (47 g) in a mixture of methanol (75 ml) and dichloromethane (15 ml). After the addition was complete, the mixture was stirred at ambient temperature for 2.5 hours, then poured onto ice-water (500 ml). The aqueous layer was separated and washed with dichloromethane (3×100 ml), then the combined organic solutions were washed with saturated aqueous sodium hydrogen carbonate solution (2×100 ml) and water (100 ml), dried (CaCl$_2$), and the solvents removed in vacua. The residue was distilled to give 2-bromo-1-[1-(3,4-dichlorophenyl)cyclobutyl] ethanone as a pale yellow oil (40.2 g), b.p. 156–164° C. at 0.8 mbar.

A solution of imidazolidine-2-thione (4.5 g) in acetone (750 ml ) was added to a solution of 2-bromo-1-[1-(3,4-dichlorophenyl)cyclobutyl]ethanone (15 g) in acetone (125 ml), then the stirred mixture was heated under reflux for 10 minutes, and allowed to cool to ambient temperature. The resulting solid was collected by filtration, washed with ethanol (50 ml) and dried in vacuo at 60° C. for 4 hours to give 1-[1-(3,4-dichlorophenyl)cyclobutyl]-2-(2-imidazolin-2-ylthio)ethanone hydrobromide as a white solid (16.3 g), m.p. 156–158° C.

A stirred suspension of 1-[1-(3,4-dichlorophenyl) cyclobutyl]-2-(2-imidazolin-2-ylthio)ethanone hydrobromide (5 g) in acetic acid (20 ml) was heated under reflux for 18 hours then allowed to cool to ambient temperature. The solvent was removed in vacuo, the residue was allowed to stand at ambient temperature for 24 hours, and the resulting solid was triturated with ether (50 ml), collected by filtration, washed with ether (50 ml) and dried in vacuo at 50° C. for 3 hours to give 3-[1-(3,4-dichlorophenyl) cyclobuty]-5,6-dihydroimidazo[2,1-b]thiazole hydrobromide as a white solid (4.5 g), m.p. 241–244° C.

EXAMPLE 2

A solution of 1-(4-chlorophenyl)cyclobutanecarbonitrile (238 g) in ether (500 ml) was added at reflux temperature under nitrogen over 40 minutes to stirred ethereal methylmagnesium iodide solution (3M; 701 ml). After the addition was complete, the mixture was stirred at reflux temperature for 3 hours and at ambient temperature for 60 hours. The resulting solid was collected by filtration, washed well with ether, and added in portions to a stirred mixture of crushed ice (1 l) and concentrated hydrochloric acid (1 l). The resulting mixture was stirred at 95° C. for 1 hour then cooled to ambient temperature. The product was extracted into dichloromethane (3×250 ml), and the combined extracts were washed with water (3×200 ml), dried (MgSO$_4$), and the solvent was removed in vacuo. The residue was distilled to give 1-[1-(4-chlorophenyl)cyclobutyl]ethanone as a brown oil (198.1 g), b.p. 95–100° C. at 0.3 mbar.

A solution of bromine (35 ml) in chloroform (150 ml) was added dropwise over 3 hours to a stirred mixture of 1-[1-(4-chlorophenyl)cyclobutyl]ethanone (150 g), chloroform (50 ml) and methanol (235 ml). When the addition was complete, the mixture was stirred at ambient temperature for a further 3 hours, then it was diluted with ice-cold water (750 ml). The product was extracted into dichloromethane (3×200 ml), and the combined extracts were washed with saturated aqueous sodium hydrogen carbonate solution (3×100 ml) and water (100 ml), dried (MgSO$_4$), and the solvents removed in vacuo, to leave 2-bromo-1-[1-(4-chlorophenyl) cyclobutyl]ethanone as an oil which was used without further purification.

A solution of 2-bromo-1-[1-(4-chlorophenyl)cyclobutyl] ethanone (2.9 g) in acetone (25 ml) was added to a solution of 3,4,5,6-tetrahydropyrimidine-2-thiol (1.2 g) in acetone (150 ml), then the mixture was heated under reflux for 1 hour, and allowed to cool to ambient temperature. The resulting solid was collected by filtration and dried in vacuo at ambient temperature to give 1-[1-(4-chlorophenyl) cyclobutyl]-2-(3,4,5,6-tetrahydropyrimidin-2-ylthio) ethanone hydrobromide as a white solid (3.5 g), m.p. 205° C.

A suspension of 1-[1-(4-chlorophenyl)cyclobutyl]-2-(3,4,5,6-tetrahydropyrimidin-2-ylthio)ethanone hydrobromide (3.4 g; prepared in a similar manner to that described above) in acetic acid (8.5 ml) was heated under reflux for 16 hours, then allowed to cool to ambient temperature. The solvent was removed in vacuo, the residue was triturated with ether (50 ml), and the resulting solid was collected by filtration, washed with ether (50 ml), and dried in vacuo at ambient temperature to give 3-[1-(4-chlorophenyl)cyclobutyl]-6,7-dihydro-5H-thiazolo[3,2-a]pyrimidine hydrobromide as a white solid (3.0 g), m.p. 256° C.

EXAMPLE 3

A solution of 2-bromo-1-[1-(4-chlorophenyl)cyclobutyl] ethanone (2.9 g) in acetone (25 ml) was added to a solution of imidazolidine-2-thione (10 g) in acetone (150 ml), then the mixture was heated under reflux for 1.5 hours, and allowed to cool to ambient temperature. The resulting solid was collected by filtration and dried in vacuo at ambient temperature to give 1-[1-(4-chlorophenyt)cyclobutyl]-2-(2-imidazolin-2-ylthio)ethanone hydrobromide as a white solid (2.3 g), m.p. 151–153° C.

A suspension of 1-[1-(4-chlorophenyl)cyclobutyl]-2-(2-imidazolin-2 ylthio)ethanone hydrobromide (2.4 g—prepared in a manner similar to that described above) in acetic acid (6 ml) was heated under reflux for 16 hours, then allowed to cool to ambient temperature. The solvent was removed in vacuo, the residue was triturated with ether (50 ml), and the resulting solid was collected by filtration, washed with ether (50 ml), dried in vacuo at ambient temperature, and recrystallised from methanol. The resulting solid was collected by filtration and dried in vacuo at ambient temperature to give 3-[1-(4-chlorophenyl) cyclobutyl]-5,6-dihydroimidazo-[2,1-b]thiazole hydrobromide as a white solid (1.4 g), m.p. 258–260° C.

EXAMPLE 4

A solution of 2-bromo-1-[1-(3,4-dichlorophenyl) cyclobutyl]ethanone (3.2 g) in acetone (25 ml) was added to a solution of 3,4,5,6-tetrahydropyrimidine-2-thiol (1.2 g) in acetone (150 mL), then the mixture was heated under reflux for 0.5 hour, and allowed to cool to ambient temperature. The resulting solid was collected by filtration and dried in vacuo at ambient temperature to give 1-[1-(3,4-dichlorophenyl)cyclobutyl]-2-(3,4,5,6-tetrahydropyrimidin-2-ylthio)ethanone hydrobromide as a white solid (3.9 g), m.p. 203–204° C.

A suspension of 1-[1-(3,4-dichlorophenyl)cyclobutyl]-2-(3,4,5,6-tetrahydropyrimidin-2-ylthio)ethanone hydrobromide (2.0 g—prepared in a manner similar to that described above) in acetic acid (7 ml) was heated under reflux for 16 hours, then allowed to cool to ambient temperature. The solvent was removed in vacuo, the residue was triturated with ether (50 ml), and the resulting solid was collected by filtration, washed with ether (50 ml), and dried in vacuo at ambient temperature to give 3-[1-(3,4-dichlorophenyl) cyclobutyl]-6,7-dihydro-5H-thiazolo[3,2-a]pyrimidine hydrobromide as a white solid (1.7 g), m.p. 269° C.

EXAMPLE 5

A solution of 2-naphthylacetonitrile (10 g) and 1,3-dibromopropane (144 g) in a mixture of ether (350 ml) and dimethylsulphoxide (150 ml) was added dropwise at 20–25° C. under nitrogen over 2 hours to a stirred mixture of finely-powdered potassium hydroxide (150 g), 18-Crown-6 (1.3 g) and dimethylsulphoxide (570 ml). After the addition was complete, the mixture was cooled to 15° C. and quenched by the slow addition of water (330 ml). Ether (330 ml) was added, and the mixture was filtered through Hyflo Supercel filtration aid. The filter pad was washed well with ether, then the aqueous layer of the filtrate was separated, diluted with water (500 ml), and washed well with ether. All of the ethereal solutions were combined, washed with water (3×100 ml), and the solvents were removed in vacua. The residue was triturated with ethanol (100 ml) and the resulting solid was collected by filtration and dried in vacua to give 1-(2-naphthyl)cyclobutanecarbonitrile as a white solid (48.7 g), which was used without further purification.

A solution of 1-(2-naphthyl)cyclobutanecarbonitrile (48.2 g) in toluene (100 ml) was added dropwise under nitrogen to a stirred solution of methylmagnesium iodide [prepared in the usual manner from iodomethane (22 ml) and magnesium (8.16 g)] in ether (60 ml), then the mixture was stirred at ambient temperature for 18 hours. The resulting solid was collected by filtration, washed with ether (50 ml), and added in portions to a mixture of concentrated hydrochloric acid (125 ml) and water (200 ml). The mixture was heated at 100° C. with occasional stirring for 10 minutes, then it was cooled to ambient temperature. The product was extracted into toluene (3×200 ml), then the extracts were washed with water (200 ml), and the solvent was removed in vacua. The residue was triturated with petroleum ether (b.p. 40–60° C.) (100 ml), and the resulting solid was collected by filtration and dried in vacuo to give 1-[1-(2-naphthyl)cyclobutyl] ethanone as a yellow solid (35 g) which was used without further purification.

Bromine (2.6 ml) was added dropwise over 1 hour at ambient temperature to a stirred solution of 1-[1-(2-naphthyl)cyclobutyl]ethanone (11.25 g) in ether (300 ml). After the addition was complete and the bromine colour had dissipated, the mixture was stirred at ambient temperature for a further 0.5 hour then it was washed with water (100 ml), saturated aqueous sodium hydrogen carbonate solution (2×100 ml) and water (100 ml), dried (MgSO$_4$), and the solvent removed in vacuo to give 2-bromo-1-[1-(2-naphthyl)cyclobutyl]ethanone as an oil which was used without purification.

A mixture of the crude 2-bromo-1-[1-(2-naphthyl) cyclobutyl]ethanone described above, imidazolidine-2-thione (5.1 g), ethanol (60 ml) and acetic acid (40 ml) was heated under reflux for 18 hours then allowed to cool to ambient temperature. The solvents were removed in vacuo and the residue was triturated with a hot mixture of ethyl acetate (100 ml) and acetone (20 ml). The resulting solid was collected by filtration, washed with ethyl acetate (50 ml), dried in vacuo at 60° C., then crystallised from ethanol. The resulting solid was collected by filtration, washed with ethanol (30 ml), and dried in vacuo at 60° C. to give 3-[1-(2-naphthyl)cyclobutyl]-5,6-dihydroimidazo[2,1-b]thiazole hydrobromide as pale yellow prisms (10 g), m.p. 239–241° C.

EXAMPLE 6

1,4-Dibromobutane (106 ml) was added dropwise over 1 hour at 70–80° C. under nitrogen to a stirred mixture of 3,4-dichlorophenylacetonitrile (150 g), benzyltriethylammonium chloride (2 g) and 50% aqueous sodium hydroxide solution (300 ml). When the addition was complete the mixture was stirred at 70–80° C. for 2 hours, then it was cooled to ambient temperature. Ether (400 ml) and water (200 ml) were added, and the layers were separated. The aqueous phase was washed with ether (2×200 ml), then the combined ethereal solutions were dried (MgSO$_4$) and the solvent was removed in vacuo. The residue was distilled to give 1-(3,4-ichlorophenyl)cyclopentanecarbonitrile as a pale yellow oil (135 g), b.p. 132–140° C./0.4 mbar.

Methylmagnesium iodide (3M solution in ether; 100 ml) was added dropwise at 0° C. under nitrogen to a stirred solution of 1-(3,4-dichlorophenyl)cyclopentanecarbonitrile (48 g) in ether (100 ml), then the mixture was stirred at ambient temperature for 24 hours. The resulting solid was collected by filtration, washed well with ether, and added in portions to an ice-cold mixture of water (200 ml) and concentrated hydrochloric acid (125 ml). The mixture was heated at 95° C. with occasional stirring for 1 hour, then it was allowed to cool to ambient temperature. The product was extracted into ether (5×100 ml), then the combined extracts were washed with water (2×100 ml), dried (MgSO$_4$), and the solvent was removed in vacuo. The residue was distilled to give 1-[1-(3,4-dichlorophenyl) cyclopentyl]ethanone as a pale yellow oil (31.9 g), b.p. 124–128° C/0.5 mbar.

A solution of bromine (6.1 ml) in dichloromethane (50 ml) was added dropwise over 3 hours at 10–15° C. under nitrogen to a stirred solution of 1-[1-(3,4-dichlorophenyl) cyclobuty]ethanone (31.9 g) in a mixture of methanol (60 ml) and dichloromethane (10 ml). When the addition was complete, the mixture was stirred at ambient temperature for 2.5 hours, then it was poured into an excess of ice-water. The product was extracted into dichloromethane (3×100 ml), then the combined extracts were washed with saturated aqueous sodium hydrogen carbonate solution (2×100 ml) followed by water (100 ml), dried (CaCl$_2$), and the solvent removed in vacuo. The residue was distilled, and the fraction of b.p. >174° C./1.3 mbar was collected and redistilled. Material of b.p. >182° C./2.6 mbar in this second distillation was collected and redistilled to give 2-bromo-1-[1-(3,4-dichlorophenyl)cyclopentyl]ethanone as a pale yellow oil (11.8 g), b.p. 156–162° C./0.4 mbar.

A mixture of 2-bromo-1-[1-(3,4-dichlorophenyl) cyclopentyl]ethanone (0.5 g), imidazolidine-2-thione (0.16 g), ethanol (3 ml) and acetic acid (2 ml) was heated under reflux for 18 hours then allowed to cool to ambient temperature. The solvents were removed in vacuo and the residue crystallised from a 1:1 mixture of ethyl acetate and ethanol. The resulting product was collected by filtration, washed with ethanol (3 ml) and dried in vacuo at 60° C. to give 3-[1-(3,4-dichlorophenyl)cyclopentyl]-5,6-dihydroimidazo[2,1-b]thiazole hydrobromide as white microneedles (0.27 g), m.p. 230–232° C.

EXAMPLE 7

A solution of 1-(4-chlorophenyl)cyclobutanecarbonitrile (35 g) in toluene (100 ml) was added dropwise at reflux temperature under nitrogen to a stirred solution of phenethylmagnesium bromide [prepared in the usual manner from phenethyl bromide (45.6 g) and magnesium (6.24 g)] in ether (100 ml). When the addition was completed, ether was distilled from the mixture until the internal temperature rose to 110° C., then stirring at this temperature was continued for 18 hours. The mixture was then cooled to ambient temperature, added to a mixture of ice (200 g) and concentrated hydrochloric acid (100 ml), heated at 95° C. with occasional stirring for 4 hours, and cooled to ambient temperature. The product was extracted into dichloromethane (3×200 ml), and the combined extracts were washed with water (100 ml), saturated aqueous sodium carbonate solution (2×100 ml) and water (100 ml), dried (Na$_2$SO$_4$), and the solvent was removed in vacuo. The residue was distilled to give 1-[1-(4-chlorophenyl) cyclobutyl]-3-phenylpropan-1-one as a yellow oil (38.8 g), b.p. 178–181° C./1.3 mbar.

Bromine (0.52 ml) was added dropwise over 20 minutes at ambient temperature to a stirred solution of 1-[1-(4-chlorophenyl)cyclobutyl]-3-phenylpropan-1-one (3 g) in ether (50 ml). After the addition was complete and the bromine colour had dissipated, the mixture was stirred at ambient temperature for a further 1 hour then it was washed with water (30 ml), saturated aqueous sodium hydrogen carbonate solution (2×30 ml) and water (30 ml), dried (MgSO$_4$), and the solvent removed in vacuo to give 2-bromo-1-[1-(4-chlorophenyl)cyclobutyl]-3-phenylpropan-1-one as an oil which was used without purification.

A mixture of the crude 2-bromo-1-[1-(4-chlorophenyl) cyclobutyl]-3-phenylpropan-1-one described above, imidazolidine-2-thione (1.02 g), ethanol (15 ml) and acetic acid (10 ml) was heated under reflux for 18 hours then allowed to cool to ambient temperature. The solvents were removed in vacuo and the residue was dried by azeotropic distillation with ethanol (50 ml) followed by ethyl acetate (50 ml). The solid remaining after removal of residual solvent in vacuo was crystallised from ethanol. The resulting product was collected by filtration, washed with ethanol (10 ml) and dried in vacuo at 60° C. to give 2-benzyl-3-[1-(4-chlorophenyl)cyclobutyl]-5,6-dihydroimidazo[2,1-b]-thiazole hydrobromide as white microneedles (2 g), m.p. 255–257° C.

EXAMPLE 8

A solution of 1-(3,4-dichlorophenyl) cyclobutanecarbonitrile (15 g) in ether (50 ml) was added dropwise to a stirred solution of 3-methoxypropylmagnesium bromide [prepared in the usual manner from 1-bromo-3-methoxypropane (15.3 g) and magnesium (2.4 g)] in ether (55 ml), then the mixture was stirred at reflux temperature for 2.5 hours, cooled to ambient temperature, and added to a mixture of crushed ice (100 g) and concentrated hydrochloric acid (80 ml). The resulting mixture was heated at 95° C. with occasional stirring for 1.5 hours, then it was allowed to stand at ambient temperature for 48 hours. The product was extracted into ether (3×100 ml), and the combined extracts were washed with water (100 ml), saturated aqueous sodium hydrogen carbonate solution (100 ml) and water (100 ml), dried (MgSO$_4$), and the solvent was removed in vacua. The residue was distilled to give 1-[1-(3,4-dichlorophenyl)cyclobutyl]-4-methoxybutanone as a pale yellow oil (16.4 g), b.p. 138–147° C./0.5 mbar.

Bromine (0.35 ml) was added dropwise over 20 minutes at ambient temperature to a stirred solution of 1-[1-(3,4-dichlorophenyl)cyclobutyl]-4-methoxybutan-1-one (2 g) in ether (40 ml). After the addition was complete and the bromine colour had dissipated, the mixture was stirred at ambient temperature for a further 1 hour then it was washed with water (30 ml), saturated aqueous sodium hydrogen carbonate solution (2×30 ml) and water (30 ml), dried (MgSO$_4$), and the solvent removed in vacuo to give 2-bromo-1-[1-(3,4-dichlorophenyl)cyclobutyl]-4-methoxybutan-1-one as an oil which was used without purification.

A mixture of the crude 2-bromo-1-[1-(3,4-dichlorophenyl)cyclobutyl]-4-methoxybutan-1-one described above, imidazolidine-2-thione (0.68 g), ethanol (15 ml) and acetic acid (10 ml) was heated under reflux for 18 hours then allowed to cool to ambient temperature. The solvents were removed in vacua and the residue was dried by azeotropic distillation with ethanol (50 ml) followed by ethyl acetate (20 ml). The solid remaining after removal of residual solvent in vacuo was crystallised from a 2:1 mixture of ethanol and ethyl acetate. The resulting product was collected by filtration, washed with ethanol (10 ml) and dried in vacuo at 60°0 C. to give 3-[1-(3,4-dichlorophenyl) cyclobutyl]-2-(2-methoxyethyl)-5,6-dihydroimidazo[2,1-b]-thiazole hydrobromide as colourless prisms (1.39 g), m.p. 227–229° C.

EXAMPLE 9

A solution of 1-(3,4-dichlorophenyl) cyclobutanecarbonitrile (6.56 g) in toluene (100 ml) was added dropwise under nitrogen to a stirred solution of benzylmagnesium chloride [prepared in the usual manner from benzyl chloride (5 ml) and magnesium (1.08 g)] in ether (100 ml). When the addition was complete, ether was distilled from the mixture until the internal temperature rose to 95° C., then the mixture was stirred at this temperature for 19 h, cooled to ambient temperature, and quenched by the dropwise addition of water (30 ml) followed by concentrated hydrochloric acid (10 ml). The mixture was stirred at 95° C. for 2.5 hours, then it was cooled to ambient temperature. The organic phase was separated, washed with water (2×100 ml) and saturated brine (100 ml), dried (Na$_2$SO$_4$), and the solvent was removed in vacuo. The residue was purified via flash chromatography over silica using a 5:95 mixture of ethyl acetate and toluene as eluant. Appropriate fractions were combined and the solvents removed in vacuo to give 1-[1-(3,4-dichlorophenyl)cyclobutyl]-2-phenyl)ethanone]-2-phenylethanone as a colourless oil (5.08 g) which solidified slowly at ambient temperature to give a colourless solid, m.p. 53–55° C.

Phenyltrimethylammonium tribromide (4.02 g) was added in portions at –10° C. to a stirred solution of 1-[1-(3,4-dichlorophenyl)cyclobutyl]-2-phenylethanone (3.41 g) in tetrahydrofuran (100 ml). The mixture was stirred at ambient temperature for 4 hours, then it was filtered, and the solvent removed in vacuo. The residue was purified via flash chromatography over silica using a 3:97 mixture of ethyl acetate and petroleum ether (b.p. 60–80° C.) as eluant. Appropriate fractions were combined, and the solvents removed in vacuo to give 2-bromo-1-[1-(3,4-dichlorophenyl)cyclobutyl]-2-phenylethanone as a colourless oil (3.8 g).

A mixture of 2-bromo-1-[1-(3,4-dichlorophenyl) cyclobutyl]-2-phenylethanone (3.8 g), imidazolidine-2-thione (0.97 g), ethanol (70 ml) and acetic acid (40 ml) was heated under reflux for 20 hours then allowed to cool to ambient temperature. The solvents were removed in vacuo and the residue was crystallised from ethanol. The resulting product was collected by filtration, washed with ethanol (10 ml) and dried in vacuo at 100° C. to give 3-[1-(3,4-dichlorophenyl)cyclobutyl]-2-phenyl-5,6-dihydroimidazo [2,1-b]thiazole hydrobromide as a pale brown solid (1.43 g), m.p. 280° C. (decomposes).

EXAMPLE 10

A solution of 1-(3,4-dichlorophenyl) cyclobutanecarbonitrile (6.56 g) in toluene (100 ml) was added dropwise under nitrogen to a stirred solution of 4-chlorobenzylmagnesium chloride [prepared in the usual manner from 4-chlorobenzyl chloride (9.07) and magnesium (1.08 g)] in ether (100 ml). When the addition was complete, ether was distilled from the mixture until the internal temperature rose to 95° C., then the mixture was stirred at this temperature for 19 h, cooled to ambient temperature, and quenched by the dropwise addition of water (50 ml) followed by concentrated hydrochloric acid (10 ml). The mixture was stirred at 95° C. for 3 hours, then it was cooled to ambient temperature. The organic phase was separated, washed with water (100 ml) and saturated brine (100 ml), dried ($Na_2SO_4$), and the solvent was removed in vacuo. The residue was purified via flash chromatography over silica using 1:9–1:4 mixtures of ethyl acetate and petroleum ether (b.p. 60–80° C.) as eluant. Appropriate fractions were combined and the solvents removed in vacuo to give 2-(4-chlorophenyl)-1-[1-(3,4-dichlorophenyl)cyclobutyl] ethanone as a yellow oil (7.51 g) which solidified slowly at ambient temperature to give a yellow solid, m.p. 82–84° C.

Phenyltrimethylammonium tribromide (6.59 g) was added in portions at –5° C. to a stirred solution of 2-(4-chlorophenyl)-1-[1-(3,4-dichlorophenyl)cyclobutyl] ethanone (6.2 g) in tetrahydrofuran (150 ml). The mixture was stirred at ambient temperature for 4 hours, allowed to stand at ambient temperature for a further 48 hours, then it was filtered, and the solvent removed in vacuo. The residue was purified via flash chromatography over silica using a 3:97 mixture of ethyl acetate and petroleum ether (b.p. 60–80° C.) as eluant. Appropriate fractions were combined, and the solvents removed in vacuo. The residue was triturated with petroleum ether (b.p. 60–80° C.) (30 ml) and the resulting solid was collected by filtration and dried in vacuo at ambient temperature to give 2-bromo-2-(4-chlorophenyl) 1-[1-(3,4-dichlorophenyl)cyclobutyl]ethanone as a colourless solid (4.83 g), m.p. 109–110° C.

A mixture of 2-bromo-2-(4-chlorophenyl)1-[1-(3,4-dichlorophenyl)cyclobutyl]ethanone (3.68 g), imidazolidine-2-thione (0.87 g), ethanol (60 ml) and acetic acid (35 ml) was heated under reflux for 18 hours then allowed to cool to ambient temperature. The solvents were removed in vacuo and the residue was triturated with ethanol (30 ml). The resulting solid was collected by filtration and crystallised from acetic acid. The resulting product was collected by filtration, washed with acetic acid (10 ml) and dried in vacuo at 100° C. to give 2-(4-chlorophenyl)-3-[1-(3,4-dichlorophenyl)cyclobutyl]-5,6-dihydroimidazo[2,1-b] thiazole hydrobromide as a colourless solid (0.93 g), m.p. 302–304° C. (decomposes).

EXAMPLE 11

A solution of 3,4-dichlorophenylacetonitrile (50 g) and iodomethane (37 ml) in ether (to total volume 220 ml) was added dropwise at ambient temperature over 3 hours to a stirred mixture of finely-powdered potassium hydroxide (68.3 g), 18-Crown-6 (0.65 g) and dimethyl sulphoxide (220 ml). When the addition was complete, the mixture was stirred at 30° C. for 2 hours, cooled to 15° C., and quenched at that temperature by the dropwise addition of water (185 ml). The product was extracted into ether (3×300 ml), and the combined extracts were washed with water (200 ml), 5M hydrochloric acid (200 ml), water (200 ml) and saturated brine (200 ml), dried ($MgSO_4$), and the solvent was removed in vacuo. The residue was distilled to give 2-(3,4-dichlorophenyl)-2-methylpropionitrile as a pale yellow oil (37.6 g), b.p. 116–120° C./2.7–3.3 mbar.

A solution of 2-(3,4-dichlorophenyl)-2-methylpropionitrile (12.8 g) in ether (100 ml) was added dropwise at –10° C. under nitrogen over 20 minutes to stirred ethereal methylmagnesium iodide solution (3M; 30 ml), then the mixture was stirred at reflux temperature for 2 hour and at ambient temperature for 18 hours. The resulting solid was collected by filtration, washed well with ether, and added in portions to a mixture of ice-cold water (100 ml) and concentrated hydrochloric acid (50 ml). The resulting mixture was heated at 95° C. with occasional stirring for 1 hour, then cooled to ambient temperature. The product was extracted into dichloromethane (3×100 ml), then the combined extracts were dried ($CaCl_2$), and the solvents were removed in vacuo to give 3-(3,4-dichlorophenyl)-3-methylbutan-2-one as a pale brown oil (9.07 g) which was used without further purification.

A solution of bromine (1.84 ml) in ether (25 ml) was added dropwise over 1 hour at ambient temperature to a stirred solution of 3-(3,4-dichlorophenyl)-3-methylbutan-2-one (8.24 g) in ether (250 ml). After the addition was complete and the bromine colour had dissipated, the mixture was stirred at ambient temperature for a further 30 minutes then it was washed with water (100 ml), saturated aqueous sodium hydrogen carbonate solution (2×100 ml) and water (100 ml), dried ($MgSO_4$), and the solvent removed in vacuo to give 1-bromo-3-(3,4-dichlorophenyl)-3 methylbutan-2-one as an oil (9.57 g) which was used without purification.

A mixture of the crude 1-bromo-3-(3,4-dichlorophenyl)-3-methylbutan-2-one described above (3.1 g), imidazolidine-2-thione (1.2 g), ethanol (1.02 ml) and acetic acid (8 ml) was heated under reflux for 22 hours then allowed to cool to ambient temperature. The solvents were removed in vacuo and the residue was triturated with hot ethyl acetate (80 ml). The resulting solid was collected by filtration, washed with ethyl acetate (20 ml), dried in vacuo at 50° C., then crystallised from ethanol. The resulting product was collected by filtration, washed with ethanol (5 ml) and dried in vacuo at 50° C. to give 3-[1-(3,4-dichlorophenyl)-1-methylethyl]-5,6-dihydroimidazo[2,1-b]-thiazole hydrobromide as an off-white solid (0.95 g), m.p. 266–270° C. (decomposes).

EXAMPLE 12

A mixture of benzo[b]thiophen-2-methanol (32.8 g) and thionyl chloride (29.7 g) was heated under reflux under nitrogen for 2-chloromethylbenzo[b]thiophene as a yellow oil (23.8 g), b.p. 108–110° C./1.4 mbar.

A mixture of 2-chloromethylbenzo[b]thiophene (21 g), potassium cyanide (11.7 g), 1,4-dioxane (200 ml) and water (100 ml) was stirred and heated under reflux for 4 hours, then cooled to ambient temperature and diluted with water (200 ml). The product was extracted into toluene (3×200 ml), then the combined extracts were washed with water (2×300 ml), dried ($Na_2SO_4$), and the solvents were removed in vacuo. The residue was purified via flash chromatography over silica using a 1:4 mixture of ethyl acetate and petroleum ether (b.p. 60–80° C.) as eluant. Appropriate fractions were combined and the solvents were removed in vacuo to give benzo[b]thiophen-2-acetonitrile as a yellow solid (8.9 g), m.p. 59–61° C.

A solution of benzo[b]thiophen-2-acetonitrile (8.05 g) and 1,3-dibromopropane (5.2 ml) in ether (50 ml) was added dropwise under nitrogen over 1 hour to a stirred, ice-cold suspension of finely-powdered potassium hydroxide (13.53 g) in dimethyl sulphoxide (100 ml). When the addition was complete, the mixture was stirred at ambient temperature for 4 hours, then it was added to ice-cold water (200 ml). The resulting mixture was acidified to pH4 by the addition of concentrated hydrochloric acid, then the product was extracted into ether (3×200 ml). The combined extracts were washed with water (500 ml), dried ($MgSO_4$), and the solvent was removed in vacuo to give 1-(benzo[b]thiophen-2-yl) cyclobutanecarbonitrile as a red oil (8.16 g) which was used without purification.

A solution of 1-(benzo[b]thiophen-2-yl) cyclobutanecarbonitrile (7.7 g) in ether (50 ml) was added dropwise at ambient temperature under nitrogen to stirred ethereal methylmagnesium iodide solution (3M; 18 ml). When the addition was complete, the mixture was stirred at reflux temperature for 3.5 hours, then it was cooled to ambient temperature. The resulting solid was collected by filtration, washed well with ether, and added in portions to 5M hydrochloric acid (143 ml). The resulting mixture was heated at 95° C. with occasional stirring for 1.5 hours, then allowed to stand at ambient temperature for 18 h. The product was extracted into dichloromethane (3×200 ml), then the combined extracts were washed with water (2×400 ml) and saturated aqueous sodium hydrogen carbonate solution (400 ml), dried ($Na_2SO_4$), and the solvent removed in vacuo to give 1-[1-(benzo[b]thiophen-2 yl)cyclobutyl] ethanone as a brown oil (5 g) which was used without purification.

Phenyltrimethylammonium tribromide (1.72 g) was added in portions at −20° C. to a stirred solution of 1-[1-(benzo[b]thiophen-2-yl)cyclobutyl]ethanone (1.05 g) in tetrahydrofuran (50 ml). The mixture was stirred at ambient temperature for 3 hours, then it was filtered, and allowed to stand at ambient temperature for a further 18 hours. The mixture was filtered once more, and the solvent was removed in vacuo. The residue was purified via flash chromatography over silica using a 1:49 mixture of ether and petroleum ether (b.p. 40–60° C.) as eluant. Appropriate fractions were combined, and the solvents removed in vacuo to give 1-[1-(benzo[b]thiophen-2-yl)cyclobutyl]-2-bromoethanone as an oil (0.46 g).

A mixture of 1-[1-(benzo[b]thiophen-2-yl)cyclobutyl]-2-bromoethanone (0.42 g), imidazolidine-2-thione (0.14 g), ethanol (15 ml) and acetic acid (10 ml) was heated under reflux for 18 hours then allowed to cool to ambient temperature. The solvents were removed in vacuo and the residue was triturated with ether (30 ml). The resulting solid was collected by filtration, dried in vacuo at 40° C. and crystallised from ethanol. The resulting product was collected by filtration, washed with ethanol (3 ml) and dried in vacuo at 40° C. to give 3-[1-(benzo[b]thiophen-2-yl)cyclobutyl]-5,6-dihydroimidazo[2,1-b]thiazole hydrobromide as an off-white solid (0.28 g), m.p. 240–242° C.

EXAMPLES 13–55

General Procedure

Aliquots of stock solutions of 2-bromo-1-[1-(3,4-dichlorophenyl)cyclobutyl]ethanone (prepared in a manner similar to that described in Example 1) or of 2-bromo-1-[1-(2-naphthyl)cyclobutyl]ethanone (prepared in a manner similar to that described in Example 5) in absolute ethanol (0.083M, 1.20 ml, 0.10 mmol) were added to a number of 20 ml screw-top vials, each containing the appropriate thiourea of Formula III (0.10 mmol) and acetic acid (0.80 ml). The reaction vials were sealed with a screw-cap and heated at 85° C. for 20 hours with agitation on an orbital shaker. Each reaction mixture was analysed by HPLC-MS and then diluted with an appropriate volume of digol so as to give a $10^{-3}$M solution of the active compound for testing in the in vitro biological assays.

The following compounds were prepared, as the major component in the reaction mixture, by the above method (HPLC purities and MS molecular ions indicated):

EXAMPLE 13

An unresolved mixture of 3-[1-(3,4-dichlorophenyl)cyclobutyl]-5-methyl-5,6-dihydroimidazo[2,1-b]thiazole hydrobromide and 3-[1-(3,4-dichlorophenyl)cyclobutyl]-6-methyl-5,6-dihydroimidazo[2,1-b]thiazole hydrobromide, HPLC 97.6% (3.17 min); m/z 339 ($MH^+$).

EXAMPLE 14

4-[1-(3,4-Dichlorophenyl)cyclobutyl]-3-methyl-2-methylimino-2,3 dihydrothiazole hydrobromide, HPLC 92.4% (3.03 min); m/z 327 ($MH^+$).

EXAMPLE 15

4-[1-(3,4-Dichlorophenyl)cyclobutyl]-3-ethyl-2-ethylimino-2,3-dihydrothiazole hydrobromide, HPLC 94.3% (3.35 min); m/z 355 ($MH^+$).

EXAMPLE 16

4-[1-(3,4-Dichlorophenyl)cyclobutyl]-3-propyl-2-propylimino-2,3-dihydrothiazole hydrobromide, HPLC 88.7% (3.83 min); m/z 383 ($MH^+$).

EXAMPLE 17

4-[1-(3,4-Dichlorophenyl)cyclobutyl]-3-isopropyl-2-isopropylimino-2,3-dihydrothiazole hydrobromide, HPLC 86.0% (3.83 min); m/z 383 ($MH^+$).

EXAMPLE 18

3-Butyl-2-butylimino-4-[1-(3,4-dichlorophenyl)cyclobutyl]-2,3-dihydrothiazole hydrobromide, HPLC 85.7% (4.27 min); m/z 411 ($MH^+$).

EXAMPLE 19

4-[1-(3,4-Dichlorophenyl)cyclobutyl]-3-isobutyl-2-isobutylimino-2,3-dihydrothiazole hydrobromide, HPLC 92.1% (3.99 min); m/z 411 ($MH^+$).

EXAMPLE 20

3-Allyl-2-allylimino-4-[1-(3,4-dichlorophenyl)cyclobutyl]-2,3-dihydrothiazole hydrobromide, HPLC 86.1% (3.58 min); m/z 379 ($MH^+$).

EXAMPLE 21

4-[1-(3,4-Dichlorophenyl)cyclobutyl]-3-cyclopropylmethyl-2-cyclopropylmethylimino-2,3-dihydrothiazole hydrobromide, HPLC 67.9% (3.93 min); m/z 407 ($MH^+$).

EXAMPLE 22

3-Benzyl-2-benzylimino-4-[1-(3,4-dichlorophenyl)cyclobutyl]-2,3-dihydrothiazole hydrobromide, HPLC 90.5% (4.79 min); m/z 479 ($MH^+$).

EXAMPLE 23

4-[1-(3,4-Dichlorophenyl)cyclobutyl]-3-(4-fluorobenzyl)-2-(4-fluorobenzylimino)-2,3-dihydrothiazole hydrobromide, HPLC 89.8% (5.00 min); m/z 515 ($MH^+$).

EXAMPLE 24

4-[1-(3,4-Dichlorophenyl)cyclobutyl]-3-phenethyl-2-phenethylimino-2,3-dihydrothiazole hydrobromide, HPLC 91.4% (5.26 min); m/z 507 ($MH^+$).

EXAMPLE 25

4-[1-(3,4-Dichlorophenyl)cyclobutyl]-3-(3-pyridylmethyl)-2-(3-pyridylmethylimino)-2,3-dihydrothiazole hydrobromide, HPLC 79.4% (3.63 min); m/z 481 ($MH^+$).

EXAMPLE 26

4-[1-(3,4-Dichlorophenyl)cyclobutyl]-3-furfuryl-2-furfurylimino-2,3-dihydrothiazole hydrobromide, HPLC 92.2% (4.57 min); m/z 459 (MH$^+$).

EXAMPLE 27

4-[1-(3,4-Dichlorophenyl)cyclobutyl]-3-phenyl-2-phenylimino-2,3-dihydrothiazole hydrobromide, HPLC 86.8% (4.94 min); m/z 451 (MH$^+$).

EXAMPLE 28

4-[1-(3,4-Dichlorophenyl)cyclobutyl]-3-(p-tolyl)-2-(ptolylimino)-2,3-dihydrothiazole hydrobromide, HPLC 85.9% (5.22 min); m/z 479 (MH$^+$).

EXAMPLE 29

4-[1-(3,4-Dichlorophenyl)cyclobutyl]-3-(o-tolyl)-2-(o-tolylimino)-2,3-dihydrothiazole hydrobromide, HPLC 92.1% (5.22 min); m/z 479 (MH$^+$).

EXAMPLE 30

4-[1-(3,4-Dichlorophenyl)cyclobutyl]-3-(3-trifluoromethylphenyl)-2-(3-trifluoromethylphenylimino)-2,3-dihydrothiazole hydrobromide, HPLC 67.6% (5.16 min); m/z 587 (MH$^+$).

EXAMPLE 31

4-[1-(3,4-Dichlorophenyl)cyclobutyl]-3-(2,4-xylyl)-2-(2,4-xylylimino)-2,3-dihydrothiazole hydrobromide, HPLC 76.8% (5.47 min); m/z 507 (MH$^+$).

EXAMPLE 32

4-[1-(3,4-Dichlorophenyl)cyclobutyl]-3-(4-ethoxyphenyl)-2-(4-ethoxyphenylimino)-2,3-dihydrothiazole hydrobromide, HPLC 68.2% (5.09 min); m/z 539 (MH$^+$).

EXAMPLE 33

4-[1-(3,4-Dichlorophenyi)cyclobutyl]-3-(3,4-dimethoxyphenethyl)-2-(3,4-dimethoxyphenethylimino)-2,3-dihydnothiazole hydrobromide, HPLC 100.0% (4.05 min); m/z 627 (MH$^+$).

EXAMPLE 34

3-[1-(2-Naphthyl)cyclobutyl]-6,7-dihydro-5H-thiazolo[3,2-a]pyrimidine hydrobromide, HPLC 50.9% (3.17 min); m/z 321 (MH$^+$).

EXAMPLE 35

An unresolved mixture of 5-methyl-3-[1-(2-naphthyl)cyclobutyl]-5,6-dihydroimidazo[2,1-b]thiazole hydrobromide and 6-methyl-3-[1-(2-naphthyl)cyclobutyl]-5,6-dihydroimidazo[2,1-b]thiazole hydrobromide, HPLC 90.4% (3.15 min); m/z 321 (MH$^+$).

EXAMPLE 36

3-Methyl-2-methylimino-4-[1-(2-naphthyl)cyclobutyl]-2,3-dihydrothiazole hydrobromide, HPLC 87.1% (3.04 min); m/z 309 (MH$^+$).

EXAMPLE 37

3-Ethyl-2-ethylimino-4-[1-(2-naphthyl)cyclobutyl]-2,3-dihydrothiazole hydrobromide, HPLC 89.4% (3.39 min); m/z 337 (MH$^+$).

EXAMPLE 38

4-[-(2-Naphthyl)cyclobutyl]-3-propyl-2-propylimino-2,3-dihydrothiazole hydrobromide, HPLC 88.5% (3.82 min); m/z 365 (MH$^+$).

EXAMPLE 39

3-Isopropyl-2-isopropylimino-4-[1-(2-naphthyl)cyclobutyl]-2,3-dihydrothiazole hydrobromide, HPLC 90.2% (3.76 min); m/z 365 (MH$^+$).

EXAMPLE 40

3-Butyl-2-butylimino-4-[1-(2-naphthyl)cyclobutyl]-2,3-dihydrothiazole hydrobromide, HPLC 94.1% (4.31 min); m/z 393 (MH$^+$).

EXAMPLE 41

3-lsobutyl-2-isobutylimino-4-[1-(2-naphthyl)cyclobutyl]-2,3-dihydrothiazole hydrobromide, HPLC 51.2% (4.18 min); m/z 393 (MH$^+$).

EXAMPLE 42

3-Allyl-2-allylimino-4-[1-(2-naphthyl)cyclobutyl]-2,3-dihydrothiazole hydrobromide, HPLC 86.3% (3.56 min); m/z 361 (MH$^+$).

EXAMPLE 43

3-Cyclopropylmethyl-2-cyclopropylmethylimino4-[1-(2-naphthyl)cyclobutyl]-2,3-dihydrothiazole hydrobromide, HPLC 89.8% (3.90 min); m/z 389 (MH$^+$).

EXAMPLE 44

3-Benzyl-2-benzylimino-4-[1-(2-naphthyl)cyclobutyl]-2,3-dihydrothiazole hydrobromide, HPLC 85.8% (4.60 min); m/z 461 (MH$^+$).

EXAMPLE 45

3-(4-Fluorobenzyl)-2-(4-fluorobenzylimino)-4-[1-(2-naphthyl)cyclobutyl]-2,3-dihydrothiazole hydrobromide, HPLC 84.7% (4.87 min); m/z 497 (MH$^+$).

EXAMPLE 46

4-1-(2-Naphthyl)cyclobutyl]-3-phenethyl-2-phenethylimino-2,3-dihydrothiazole hydrobromide, HPLC 87.2% (4.99 min); m/z 489 (MH$^+$).

EXAMPLE 47

4-[1-(2-Naphthyl)cyclobutyl]-3-(3-pyridylmethyl)-2-(3-pyridylmethylimino)-2,3-dihydrothiazole hydrobromide, HPLC 68.6% (3.56 min); m/z 463 (MH$^+$).

EXAMPLE 48

3-Furfuryl-2-furfurylimino-4-[1-(2-naphthyl)cyclobutyl]-2,3-dihydrothiazole hydrobromide, HPLC 90.6% (4.44 min); m/z 441 (MH$^+$).

EXAMPLE 49

4-[1-(2-Naphthyl)cyclobutyl]-3-phenyl-2-phenylimino-2,3-dihydrothiazole hydrobromide, HPLC 87.7% (4.93 min); m/z 433 (MH$^+$).

EXAMPLE 50

4-[1-(2-Naphthyl)cyclobutyl]-3-(p-tolyl)-2-(p-tolylimino)-2,3-dihydrothiazole hydrobromide, HPLC 79.8% (5.20 min); m/z 461 (MH$^+$).

EXAMPLE 51

4-[1-(2-Naphthyl)cyclobutyl]-3-(o-tolyl)-2-(o-tolylimino)-2,3-dihydrothiazole hydrobromide, HPLC 85.1% (5.21 min); m/z 461 (MH$^+$).

EXAMPLE 52

4-[1-(2-Naphthyl)cyclobutyl]-3-(2,4-xylyl)-2-(2,4-xylylimino)-2,3-dihydrothiazole hydrobromide, HPLC 71.2% (5.44 min); m/z 489 (MH$^+$).

EXAMPLE 53

3-Cyclopentyl-2-cyclopentylimino-4-[1-(2-naphthyl)cyclobutyl]-2,3-dihydrothiazole hydrobromide, HPLC 87.4% (5.68 min); m/z 417 (MH$^+$).

EXAMPLE 54

3-(4-Ethoxyphenyl)-2-(4-ethoxyphenylimino)-4-[1-(2-naphthyl)cyclobutyl]-2,3-dihydrothiazole hydrobromide, HPLC 76.9% (5.07 min); m/z 521 (MH$^+$).

EXAMPLE 55

3-(3,4-Dimethoxyphenethyl)-2-(3,4-dimethoxyphenethylimino)-4-[1-(2-naphthyl)cyclobutyl]-2,3-dihydrothiazole hydrobromide, HPLC 89.2% (3.96 min); m/z 609 (MH$^+$).

EXAMPLES 56–76

General Procedure

Solutions of a range of ketones of Formula V (0.40 mmol) in ether (8.0 ml) were prepared in 20 ml screw-top vials. Bromine (64 mg, 0.40 mmol) was added to each solution, then the vials were sealed with screw-caps and left to stand at ambient temperature for 70 hours. The caps were removed and the solvent was removed in vacua. Each residue was then dissolved in ethanol (8 ml) and individual 1 ml aliquots of each solution, containing 0.05 mmol of the resulting bromoketone of Formula IV, were dispensed into 40 ml screw-top vials, each containing acetic acid (1.25 ml) and a solution of a thiourea of Formula III in ethanol (0.05M, 1 ml, 0.05 mmol). The vials were sealed, then heated at 85° C. for 24–29 hours with agitation on an orbital shaker. Each reaction mixture was analysed by HPLC-MS, then the solvents were removed in vacuo. The individual residues were dissolved in methanol (4.0 ml), then further diluted with an appropriate volume of digol so as to give a 10$^{-3}$M solution of the active compound for testing in the in vitro biological assays.

The following compounds were prepared, as the major component in the reaction mixture, by the above method (HPLC purities and MS molecular ions indicated):

EXAMPLE 56

3-Butyl-2-butylimino-4-[1-(4-chlorophenyl)cyclobutyl]-2,3-dihydrothiazole hydrobromide, HPLC 98.4% (4.20 min); m/z 377 (MH$^+$).

EXAMPLE 57

4-[1-(4-Bromophenyl)cyclobutyl]-3-butyl-2-butylimino-2,3-dihydrothiazole hydrobromide, HPLC 63.2% (4.27 min); m/z 421 (MH$^+$).

EXAMPLE 58

3-Butyl-2-butylimino-4-[1-(4-methylthiophenyl)cyclobutyl]-2,3-dihydrothiazole hydrobromide, HPLC 86.3% (4.15 min); m/z 389 (MH$^+$).

EXAMPLE 59

3-Butyl-2-butylimino-4-[1-(4-phenoxyphenyl)cyclobutyl]-2,3-dihydrothiazole hydrobromide, HPLC 87.2% (4.63 min); m/z 435 (MH$^+$).

EXAMPLE 60

3-Butyl-2-butylimino-4-[1-(4-chlorophenyl)cyclopentyl]-2,3-dihydrothiazole hydrobromide, HPLC 70.1% (4.41 min); m/z 391 (MH$^+$).

EXAMPLE 61

3-Butyl-2-butylimino-4-(1-phenylcyclohexyl)-2,3-dihydrothiazole hydrobromide, HPLC 73.4% (4.52 min); m/z 371 (MH$^+$).

EXAMPLE 62

3-Butyl-2-butylimino-4-[1-(4-chlorophenyl)-1-methylethyl]-2,3-dihydrothiazole hydrobromide, HPLC 93.3% (4.10 min); m/z 365 (MH$^+$).

EXAMPLE 63

3-Butyl-2-butylimino-4-[1-(3,4-dichlorophenyl)-1-methylethyl]-2,3-dihydrothiazole hydrobromide, HPLC 90.7% (4.24 min); m/z 399 (MH$^+$).

EXAMPLE 64

4-[1-(4-Chlorophenyl)cyclobutyl]-3-phenethyl-2-phenethylimino-2,3-dihydrothiazole hydrobromide, HPLC 89.1% (4.84 min); m/z 473 (MH$^+$).

EXAMPLE 65

4-[1-(4-Chlorophenyl)cyclobutyl]-3-(3,4-dimethoxyphenethyl)-2-(3,4-dimethoxyphenethylimino)-2,3dihydrothiazole hydrobromide, HPLC 88.4% (3.91 min); m/z 593 (MH$^+$).

EXAMPLE 66

4-[1-(4-Bromophenyl)cyclobutyl]-3-(3,4-dimethoxyphenethyl)-2-(3,4-dimethoxyphenethylimino)-2,3-dihydrothiazole hydrobromide, HPLC 70.6% (3.99 min); m/z 637 (MH$^+$).

EXAMPLE 67

4-[1-(4-Chlorophenyl)cyclopentyl]-3-(3,4-dimethoxyphenethyl)-2-(3,4-dimethoxyphenethylimino)-2,3-dihydrothiazole hydrobromide, HPLC 90.6% (4.07 min); m/z 607 (MH$^+$).

EXAMPLE 68

3-(3,4-Dimethoxyphenethyl)-2-(3,4-dimethoxyphenethylimino)-4-(1-phenylcyclohexyl)-2,3-dihydrothiazole hydrobromide, HPLC 78.1% (4.01 min); m/z 587 (MH$^+$).

EXAMPLE 69

4-[1-(3,4-Dichlorophenyl)-1-methylethyl]-3-(3,4-dimethoxyphenethyl)-2-(3,4-dimethoxyphenethylimino)-2,3-dihydrothiazole hydrobromide, HPLC 90.6% (3.98 min); m/z 615 (MH$^+$).

EXAMPLE 70

3-[1-(4-Bromophenyl)cyclobutyl]-5,6-dihydroimidazo[2,1-b]thiazole hydrobromide, HPLC 92.3% (2.96 min); m/z 335 (MH$^+$)

EXAMPLE 71

3-[1-(4-Chlorophenyl)cyclopentyl]-5,6-dihydroimidazo[2,1-b]thiazole hydrobromide, HPLC 95.7% (3.06 min); m/z 305 (MH$^+$)

EXAMPLE 72

3-(1-Phenylcyclohexyl)-5,6-dihydroimidazo[2,1-b]thiazole hydrobromide, HPLC 85.2% (2.91 min); m/z 285 (MH$^+$)

EXAMPLE 73

3-[1-(4-Chlorophenyl)-1-methylethyl]-5,6-dihydroimidazo[2,1-b]thiazole hydrobromide, HPLC 98.1% (2.68 min); m/z 279 (MH$^+$)

EXAMPLE 74

3-[1-(3,4-Dichlorophenyl)-1-methylethyl]-5,6-dihydroimidazo[2,1-b]thiazole hydrobromide, HPLC 97.3% (2.92 min); m/z 313 (MH$^+$)

EXAMPLE 75

3-[1-(3-Fluorophenyl)cyclobutyl]-5,6-dihydroimidazo[2,1-b]thiazole hydrobromide, HPLC 95.1% (2.52 min); m/z 275 (MH$^+$)

EXAMPLE 76

3-[1-(4-Methylthiophenyl)cyclobutyl]-5,6-dihydroimidazo[2,1-b]thiazole hydrobromide, HPLC 91.0% (2.91 min); m/z 303 (MH$^+$)

EXAMPLE 77

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

What is claimed is:

1. Compounds of formula I

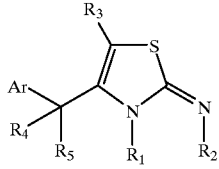

including pharmaceutically acceptable salts thereof in the form of individual enantiomers, racemates, or other mixtures of enantiomers, in which Ar is phenyl, naphthyl or benzo[b]thiophenyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) a phenoxy group optionally substituted by one or more halo or f) phenyl optionally substituted by one or more halo;

$R_1$ and $R_2$, which may be the same or different, independently are a) an alkyl group containing 1 to 6 carbon atoms, b) an alkenyl group containing 3 to 6 carbon atoms, c) a cycloalkyl group containing 3 to 7 carbon atoms, d) a cycloalkylmethyl group in which the ring contains 3 to 7 carbon atoms, e) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo, f) an arylalkyl or heteroarylalkyl group in which the alkyl chain contains 1 to 3 carbon atoms and in which the aryl or heteroaryl group may optionally be substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo; or $R_1$ and $R_2$ form an alkylene chain optionally substituted by one or more alkyl groups each containing 1 to 3 carbon atoms, such that, together with the atoms to which they are attached, they form a 5 or 6 membered ring, $R_3$ is a) H, b) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo, c) an arylmethyl group in which the aryl is optionally substituted by one or more substituents selected from i) halo, ii) an alkyl group containing 1 to 3 carbon atoms optionally substituted by one or more halo, iii) an alkoxy group containing 1 to 3 carbon atoms optionally substituted by one or more halo, iv) an alkylthio group containing 1 to 3 carbon atoms optionally substituted by one or more halo; or d) an alkoxyalkyl group containing 3 to 6 carbon atoms; and $R_4$ and $R_5$, which may be the same or different, independently are an alkyl group containing 1 to 3 carbon atoms, or $R_4$ and $R_5$ together with the atom to which they are attached form a cycloalkyl ring containing 3 to 6 carbon atoms.

2. Compounds as claimed in claim 1 in which Ar is naphthyl, benzo[b]thiophenyl or phenyl optionally substituted by one or more substituents selected from halo, an alkylthio group containing 1 to 3 carbon atoms, or a phenoxy group.

3. Compounds as claimed in claim 1 in which $R_1$ and $R_2$, which may be the same or different, independently are a) an alkyl group containing 1 to 4 carbon atoms, b) an alkenyl group containing 3 or 4 carbon atoms, c) a cycloalkyl group containing 3 to 5 carbon atoms, d) a cycloalkylmethyl group in which the ring contains 3 to 5 carbon atoms, e) an aryl or heteroaryl group optionally substituted by one or more substituents selected from i) halo, ii) an alkyl group containing 1 to 3 carbon atoms optionally substituted by one or more halo, iii) an alkoxy group containing 1 to 3 carbon atoms, f) an arylalkyl or heteroarylalkyl group in which the alkyl chain contains 1 or 2 carbon atoms and in which the aryl or heteroaryl group may optionally be substituted by one or more substituents selected from halo or an alkoxy group containing 1 to 3 carbon atoms; or $R_1$ and $R_2$ form an alkylene chain such that, together with the atoms to which they are attached, they form a 5 or 6 membered ring, optionally substituted by one or more methyl groups.

4. Compounds as claimed in claim 1 in which $R_3$ is H, an aryl or heteroaryl group optionally substituted by one or more halo, an arylmethyl group in which the aryl is optionally substituted by one or more halo, or an alkoxyalkyl group containing 3 to 6 carbon atoms.

5. Compounds as claimed in claim 1 in which $R_4$ and $R_5$, which may be the same or different, independently are methyl, or $R_4$ and $R_5$ together with the atom to which they are attached form a cycloalkyl ring containing 3 to 6 carbon atoms.

6. Compounds as claimed in claim 1 in which $R_1$ and $R_2$ are identical.

7. Compounds as claimed in claim 1 in which $R_1$ and $R_2$ form an alkylene chain such that, together with atoms to which they are attached, they form a 5 or 6 membered ring, optionally substituted by a methyl group.

8. Compounds as claimed in claim 1 in which $R_4$ and $R_5$ are identical.

9. Compounds as claimed in claim 1 in which $R_4$ and $R_5$ together with the atom to which they are attached form a cyclobutane, cyclopentane or cyclohexane ring.

10. Compounds as claimed in claim 1 as represented by Formula Ia

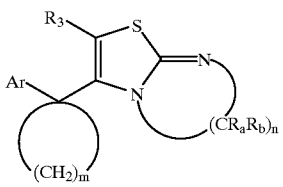

including pharmaceutically acceptable salts thereof in the form of individual enantiomers, racemates, or other mixtures of enantiomers, in which m is 2, 3 or 4;

n is 2 or 3;

Ar is phenyl or naphthyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, or e) phenyl;

$R_a$ and $R_b$ independently are H or an alkyl group containing 1 to 3 carbon atoms optionally substituted by one or more halo; and $R_3$ is H.

11. A compound selected from

3-[1-(3,4-Dichlorophenyl)cyclobutyl]-5,6-dihydroimidazo[2,1-b]thiazole;

3-[1-(4-Chlorophenyl)cyclobutyl]-6,7-dihydro-5H-thiazolo[3,2-a]pyrmidine;

3-[1-(4-Chlorophenyl)cyclobutyl]-5,6-dihydroimidazo[2,1-b]thiazole;

3-[1-(3,4-Dichlorophenyl)cyclobutyl]-6,7-dihydro-5H-thiazolo[3,2-a]pyrimidine;

3-[1-(2-Naphthyl)cyclobutyl]-5,6-dihydroimidazo[2,1-b]thiazole;

3-[1-(3,4-Dichlorophenyl)cyclopentyl]-5,6-dihydroimidazo[2,1-b]thiazole;

2-Benzyl-3-[1-(4-chlorophenyl)cyclobutyl]-5,6-dihydroimidazo[2,1-b]thiazole;

3-[1-(3,4-Dichlorophenyl)cyclobutyl]-2-(2-methoxyethyl)-5,6-dihydroimidazo[2,1-b]thiazole;

3-[1-(3,4-Dichlorophenyl)cyclobutyl]-2-phenyl-5,6-dihydroimidazo[2,1-b]thiazole;

2-(4-Chlorophenyl)-3-[1-(3,4-dichlorophenyl)cyclobutyl]-5,6-dihydroimidazo[2,1-b]thiazole;

3-[1-(3,4-Dichlorophenyl)-1-methylethyl]-5,6-dihydroimidazo[2,1-b]thiazole;

3-[1-(Benzo[b]thiophen-2-yl)cyclobutyl]-5,6-dihydroimidazo[2,1-b]thiazole;

3-[1-(3,4-Dichlorophenyl)cyclobutyl]-5-methyl-5,6-dihydroimidazo[2,1-b]-thiazole;

3-[1-(3,4-Dichlorophenyl)cyclobutyl]-6-methyl-5,6-dihydroimidazo[2,1-b]-thiazole;

4-[1-(3,4-Dichlorophenyl)cyclobutyl]-3-methyl-2-methylimino-2,3-dihydrothiazole;

4-[1-(3,4-Dichlorophenyl)cyclobutyl]-3-ethyl-2-ethylimino-2,3-dihydrothiazole;

4-[1-(3,4-Dichlorophenyl)cyclobutyl]-3-propyl-2-propylimino-2,3-dihydrothiazole;

4-[1-(3,4-Dichlorophenyl)cyclobutyl]-3-isopropyl-2-isopropylimino-2,3-dihydrothiazole;

3-Butyl-2-butylimino-4-[1-(3,4-dichlorophenyl) cyclobutyl]-2,3-dihydrothiazole;

4-[1-(3,4-Dichlorophenyl)cyclobutyl]-3-isobutyl-2-isobutylimino-2,3dihydrothiazole;

3-Allyl-2-allylimino-4-[1-(3,4-dichlorophenyl) cyclobutyl]-2,3-dihydrothiazole;

4-[1-(3,4-Dichlorophenyl)cyclobutyl]-3-cyclopropylmethyl-2-cyclopropylmethylimino]-2,3-dihydrothiazole;

3-Benzyl-2-benzylimino-4-[1-(3,4-dichlorophenyl) cyclobutyl]-2,3-dihydrothiazole;

4-[1-(3,4-Dichlorophenyl)cyclobuty]-3-(4-fluorobenzyl)-2-(4-fluorobenzylimino)-2,3-dihydrothiazole;

4-[1-(3,4-Dichlorophenyl)cyclobutyl]-3-phenethyl-2-phenethylimino-2,3-dihydrothiazole;

4-[1-(3,4-Dichlorophenyl)cyclobutyl]-3-(3-pyridylmethyl)-2-(3-pyridyimethylimino)-2,3-dihydrothiazole;

4-[1-(3,4-Dichlorophenyl)cyclobutyl]-3-furfuryl-2-furfurylimino-2,3-dihydrothiazole;

4-[1-(3,4-Dichlorophenyl)cyclobutyl]-3-phenyl-2-phenylimino-2,3-dihydrothiazole;

4-[1-(3,4-Dichlorophenyl)cyclobutyl]-3-(p-tolyl)-2-(p-tolylimino)-2,3-dihydrothiazole;

4-[1-(3,4-Dichlorophenyl)cyclobutyl]-3-(o-tolyl)-2-(o-tolylimino)-2,3-dihydrothiazole;

4-[1-(3,4-Dichlorophenyl)cyclobutyl]-3-(3-trifluoromethylphenyl)-2-(3-trifluoromethylphenylimino)-2,3-dihydrothiazole;

4-[1-(3,4-Dichlorophenyl)cyclobutyl]-3-(2,4-xylyl)-2-(2,4-xylylimino)-2,3-dihydrothiazole;

4-[1-(3,4-Dichlorophenyl)cyclobutyl]-3-(4-ethoxypheny-2-(4-ethoxyphenylimino)-2,3-dihydrothiazole;

4-[1-(3,4-Dichlorophenyl)cyclobutyl]-3-(3,4-dimethoxyphenethyl)-2-(3,4-dimethoxyphenethylimino)-2,3-dihydrothiazole;

3-[1-(2-Naphthyl)cyclobutyl]-6,7-dihydro-5H-thiazolo[3,2-a]pyrimidine;

5-Methyl-3-[1-(2-naphthyl)cyclobutyl]-5,6-dihydroimidazo[2,1-b]thiazole;

6-Methyl-3-[1-(2-naphthyl)cyclobutyl]-5,6-dihydroimidazo[2,1-b]thiazole;

3-Methyl-2-methylimino-4-[1-(2-naphthyl)cyclobutyl]-2,3-dihydrothiazole;

3-Ethyl-2-ethylimino-4-[1-(2-naphthyl)cyclobutyl]-2,3-dihydrothiazole;

4-[1-(2-Naphthyl)cyclobutyl]-3-propyl-2-propylimino-2,3-dihydrothiazole;

3-Isopropyl-2-isopropylimino-4-[1-(2-naphthyl) cyclobutyl]-2,3-dihydrothiazole;

3-Butyl-2-butylimino-4-[1-(2-naphthyl)cyclobutyl]-2,3-dihydrothiazole;

3-Isobutyl-2-isobutylimino-4-[1-(2-naphthyl) cyclobutyl]-2,3-dihydrothiazole;

3-Allyl-2-allylimino-4-[1-(2-naphthyl)cyclobutyl]-2,3-dihydrothiazole;

3-Cyclopropylmethyl-2-cyclopropylmethylimino-4-[1-(2-naphthyl)cyclobutyl]-2,3-dihydrothiazole;

3-Benzyl-2-benzylimino-4-[1-(2-naphthyl)cyclobutyl]-2,3-dihydrothiazole;

3-(4-Fluorobenzyl)-2-(4-fluorobenzylimino)-4-[1-(2-naphthyl)cyclobutyl]-2,3-dihydrothiazole;

4-[1-(2-Naphthyl)cyclobutyl]-3-phenethyl-2-phenethylimino-2,3-dihydrothiazole hydrobromide;

4-[1-(2-Naphthyl)cyclobutyl]-3-(3-pyridylmethyl)-2-(3-pyridylmethylimino)-2,3-dihydrothiazole;

3-Furfuryl-2-furfurylimino-4-[1-(2-naphthyl)cyclobutyl]-2,3-dihydrothiazole;

4-[1-(2-Naphthyl)cyclobutyl]-3-phenyl-2-phenylimino-2,3-dihydrothiazole;

4-[1-(2-Naphthyl)cyclobutyl]-3-(p-tolyl)-2-(p-tolylimino)-2,3-dihydrothiazole;

4-[1-(2-Naphthyl)cyclobutyl]-3-(o-tolyl)-2-(o-tolylimino)-2,3-dihydrothiazole;

4-[1-(2-Naphthyl)cyclobutyl]-3-(2,4-xylyl)-2-(2,4-xylylimino)-2,3-dihydrothiazole;

3-Cyclopentyl-2-cyclopentylimino-4-[1-(2-naphthyl) cyclobutyl]-2,3-dihydrothiazole;

3-(4-Ethoxyphenyl)-2-(4-ethoxyphenylimino)-4-[1-(2-naphthyl)cyclobutyl]-2,3-dihydrothiazole;

3-(3,4-Dimethoxyphenethyl)-2-(3,4-dimethoxyphenethylimino)-4-[1-(2-naphthyl) cyclobutyl]-2,3-dihydrothiazole;

3-Butyl-2-butylimino-4-[(4-chlorophenyl)cyclobutyl]-2,3-dihydrothiazole;

4-[1-(4-Bromophenyl)cyclobutyl]-3-butyl-2-butylimino-2,3-dihydrothiazole;

3-Butyl-2-butylimino-4-[1-(4-methylthiophenyl) cyclobutyl]-2,3-dihydrothiazole;

3-Butyl-2-butylimino-4-[1-(4-phenoxyphenyl) cyclobutyl]-2,3-dihydrothiazole;

3-Butyl-2-butylimino-4-[1-(4-chlorophenyl) cyclopentyl]-2,3-dihydrothiazole;

3-Butyl-2-butylimino-4-(1-phenylcyclohexyl)-2,3-dihydrothiazole;

3-Butyl-2-butylimino-4-[1-(4-chlorophenyl)-1-methylethyl]-2,3-dihydrothiazole;

3-Butyl-2-butylimino-4-[1-(3,4-dichlorophenyl)-1-methylethyl]-2,3-dihydrothiazole;

4-[1-(4-Chlorophenyl)cyclobutyl]-3-phenethyl-2-phenethylimino-2,3-dihydrothiazole;

4-[1-(4-Chlorophenyl)cyclobutyl]-3-(3,4-dimethoxyphenethyl)-2-(3,4-dimethoxyphenethylimino)-2,3-dihydrothiazole;

4-[1-(4-Bromophenyl)cyclobutyl]-3-(3,4-dimethoxyphenethyl)-2-(3,4-dimethoxyphenethylimino)-2,3-dihydrothiazole;

4-[1-(4-Chlorophenyl)cyclopentyl]-3-(3,4-dimethoxyphenethyl)-2-(3,4-dimethoxyphenethylimino)-2,3-dihydrothiazole;

3-(3,4-Dimethoxyphenethyl)-2-(3,4-dimethoxyphenethylimino)-4-(1-phenylcyclohexyl)-2,3-dihydrothiazole;

4-[1-(3,4-Dichlorophenyl)-1-methylethyl]-3-(3,4-dimethoxyphenethyl)-2-(3,4-dimethoxyphenethylimino)-2,3-dihydrothiazole;

3-[1-(4-Bromophenyl)cyclobutyl]-5,6-dihydroimidazo[2,1-b]thiazole;

3-[1-(4-Chlorophenyl)cyclopentyl]-5,6-dihydroimidazo[2,1-b]thiazole;

3-(1-Phenylcyclohexyl)-5,6-dihydroimidazo[2,1-b]thiazole;

3-[1-(4-Chlorophenyl)-1-methylethyl]-5,6-dihydroimidazo[2,1-b]thiazole;

3-[1-(3,4-Dichlorophenyl)-1-methylethyl]-5,6-dihydroimidazo[2,1-b]thiazole;

3-[1-(3-Fluorophenyl)cyclobutyl]-5,6-dihydroimidazo[2,1-b]thiazole; and

3-[1-(4-Methylthiophenyl)cyclobutyl]-5,6-dihydroimidazo[2,1-b]thiazole;

and pharmaceutically acceptable salts thereof.

12. A pharmaceutical composition comprising a therapeutically effective amount of a compound of Formula I, as claimed in claim 1, together with a pharmaceutically acceptable diluent or carrier.

13. A method of treating depression, anxiety, Parkinson's disease, obesity, cognitive disorders, seizures, and of neuroprotection to protect against stroke in human beings, comprising the administration of a therapeutically effective amount of a compound of Formula I, as claimed in claim 1, to a patient in need thereof.

14. A process for the preparation of compounds of Formula I, as claimed in claim 1, comprising heating a compound of Formula II

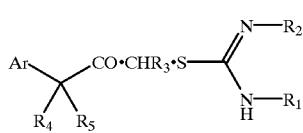

II in which Ar, $R_1$, $R_2$, $R_3$, $R_4$ and $R_5$ are as defined for Formula I in claim 1, optionally in the presence of an acid.

15. The compounds of claim 2, wherein Ar is 2-naphthyl, benzo(b)thiophen-2-yl, 4-chlorophenyl, 3-4-dichlorophenyl, 4-bromophenyl or 4-methylthiophenyl.

16. The compounds of claim 1, wherein $R_1$ and $R_2$ are a) an alkyl group containing 1 to 4 carbon atoms, b) allyl, c) cyclopentyl, d) cyclopropylmethyl, e) an aryl group optionally substituted by one or more substituents selected from i) halo, ii) methyl, iii) trifluoromethyl, iv) ethoxy, f) an arylalkyl or heteroarylalkyl group in which the alkyl chain contains 1 or 2 carbon atoms and in which the aryl or heteroaryl group may optionally be substituted by one or more substituents selected from halo or methoxy; or $R_1$ and $R_2$ form an alkylene chain such that, together with the atoms to which they are attached, they form a 5 or 6 membered ring, optionally substituted by one or more methyl groups.

17. The compounds of claim 16, wherein $R_1$ and $R_2$ are methyl, ethyl, propyl, isopropyl, butyl, isobutyl, allyl, cyclopropylmethyl, benzyl, 4-fluorobenzyl, pyrid-3-ylmethyl, furfuryl, phenethyl or 2-(3,4-dimethyloxyphenyl)ethyl; or $R_1$ and $R_2$ form an alkylene chain such that, together with the atoms to which they are attached, they form a 5 or 6 membered ring, optionally substituted by a methyl group.

18. The compounds of claim 17, wherein $R_1$ and $R_2$ are identical.

19. The compounds of claim 1, wherein $R_3$ is H, an aryl or heteroaryl group optionally substituted by one or more halo, an arylmethyl group in which the aryl is optionally substituted by one or more halo, or an alkoxyalkyl group containing 3 to 6 carbon atoms.

20. The compounds of claim 19, wherein $R_3$ is H, phenyl, 4-chlorophenyl, benzyl or 2-methoxyethyl.

21. The compounds of claim 20, wherein $R_3$ is H.

22. The compounds of claim 10, wherein m is 3, n is 2 or 3, Ar is phenyl or naphthyl, each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, or e) phenyl, $R_a$ and $R_b$ independently are H or an alkyl group containing 1 to 3 carbon atoms optionally substituted by one or more halo and $R_3$ is H.

23. The compounds of claim 22, wherein n is 2.

24. The compounds of claim 10, wherein $R_a$, $R_b$ and $R_3$ are each H.

25. The compounds of claim 22, wherein $R_a$, $R_b$ and $R_3$ are each H.

26. 3-(1-(2-naphthyl)cyclobutyl)-5,6-dihydroimidazo(2,1-b)thiazole and pharmaceutically acceptable salts thereof.

* * * * *